(12) United States Patent
Ilsen et al.

(10) Patent No.: US 6,757,898 B1
(45) Date of Patent: Jun. 29, 2004

(54) ELECTRONIC PROVIDER—PATIENT INTERFACE SYSTEM

(75) Inventors: Kevin Ilsen, Lowell, MA (US); Michael J. Cataldo, Hingham, MA (US)

(73) Assignee: McKesson Information Solutions, Inc., Alpharetta, GA (US)

(*) Notice: Subject to any disclaimer, the term of this patent is extended or adjusted under 35 U.S.C. 154(b) by 0 days.

(21) Appl. No.: 09/484,550

(22) Filed: Jan. 18, 2000

(51) Int. Cl.$^7$ .......................... G06F 15/16; A61B 5/00
(52) U.S. Cl. ...................................... 718/203; 600/300
(58) Field of Search .................. 709/203, 100–109; 707/1–199; 600/300

(56) References Cited

U.S. PATENT DOCUMENTS

| | | | | |
|---|---|---|---|---|
| 4,766,542 A | * | 8/1988 | Pilarczyk | |
| 5,099,424 A | * | 3/1992 | Schneiderman | |
| 5,193,855 A | * | 3/1993 | Shamos | 283/117 |
| 5,291,399 A | * | 3/1994 | Chaco | |
| 5,293,250 A | * | 3/1994 | Okumura et al. | |
| 5,325,294 A | * | 6/1994 | Keene | |
| 5,361,202 A | * | 11/1994 | Doue | |
| 5,548,753 A | * | 8/1996 | Linstead et al. | |
| 5,557,780 A | * | 9/1996 | Edwards et al. | |
| 5,612,733 A | * | 3/1997 | Flohr | |
| 5,612,869 A | * | 3/1997 | Letzt et al. | |
| 5,619,991 A | * | 4/1997 | Sloane | 600/300 |
| 5,644,778 A | * | 7/1997 | Burks et al. | |

(List continued on next page.)

OTHER PUBLICATIONS

DrKoop.com, 1998 [retrieved on 2000-05-24] Retrieved from the Internet:<URL:www.drkoop.com>.

(List continued on next page.)

Primary Examiner—John Follansbee
Assistant Examiner—Kenneth Tang
(74) Attorney, Agent, or Firm—Evelyn H. McConathy; Dilworth Paxson LLP

(57) ABSTRACT

The present invention provides a communication system for providing automated, electronic communications between at least one health-care provider and a plurality of users of the health-care provider, wherein the communications occur over a communications network through a provider/patient interface, said system comprising:

a central server, comprising one server or a logic unit of multiple servers;

a provider's service computer, a plurality of users' computers; and a communication network for enabling communication between and among the central server, the provider's service computer, and the plurality of users' computers. In a preferred embodiment, the communication system of the present invention is the Electronic Provider-Patient Interface (the ePPi™). The preferred users of the ePPi system are patients, and the preferred provider is the patient's own doctor or health-care practitioner. At the core of the present invention is a fully automated mechanism for generating a personalized area (patient page) for each user within the doctor's or health-care group's Web site in the ePPi system, and for introducing provider-based content to the system in standardized formats, such as standard administrative and billing codes. Thus, the ePPi system, provides an automated service to patients, through which access to their own doctor is provided over the Internet without additional work for the doctor's office. Moreover, the ePPi system offers patients access to a variety of practice-based services including, appointment requests and updates, prescription refills, online triage, health search information and the like.

18 Claims, 12 Drawing Sheets ePPi Core Functional Architecture

U.S. PATENT DOCUMENTS

| | | | | |
|---|---|---|---|---|
| 5,664,109 | A | * | 9/1997 | Johnson et al. |
| 5,706,441 | A | * | 1/1998 | Lockwood |
| 5,737,539 | A | * | 4/1998 | Edelson et al. |
| 5,758,095 | A | * | 5/1998 | Albaum et al. |
| 5,764,923 | A | * | 6/1998 | Tallman et al. |
| 5,772,585 | A | * | 6/1998 | Lavin et al. |
| 5,786,923 | A | * | 7/1998 | Doucet et al. |
| 5,845,253 | A | * | 12/1998 | Rensimer et al. |
| 5,845,255 | A | * | 12/1998 | Mayaud |
| 5,890,129 | A | * | 3/1999 | Spurgeon |
| 5,899,998 | A | * | 5/1999 | McGauley et al. ...... 707/104.1 |
| 5,924,074 | A | * | 7/1999 | Evans ........................... 705/3 |
| 5,940,843 | A | * | 8/1999 | Zucknovich et al. |
| 5,995,965 | A | * | 11/1999 | Experton ..................... 707/10 |
| 5,997,476 | A | * | 12/1999 | Brown ....................... 600/300 |
| 6,021,426 | A | * | 2/2000 | Douglis et al. |
| 6,039,688 | A | * | 3/2000 | Douglas et al. |
| 6,230,142 | B1 | * | 5/2001 | Benigno et al. ............... 705/3 |
| 6,249,809 | B1 | * | 6/2001 | Bro ............................. 709/217 |
| 6,270,456 | B1 | * | 8/2001 | Iliff ............................ 600/300 |
| 6,283,761 | B1 | * | 9/2001 | Joao ............................ 434/236 |
| 6,294,999 | B1 | * | 9/2001 | Yarin et al. .............. 340/573.1 |
| 6,368,273 | B1 | * | 4/2002 | Brown ....................... 600/300 |

OTHER PUBLICATIONS

Intellihealth, 1996 [retrieved on 2000–05–25] Retrieved from the Internet:<URL:www.intellihealth.com>.

AmericasDoctor.com, 1998 [retrieved on 2000–05–24] Retrieved from the Internet:<URL:www.americasdoctor.com>.

ChannelHealth, 1999 [retrieved on 2000–05–24] Retrieved from the Internet:<URL.www.channelhealth.com>.

Healinx, 2000 [retrieved on 2000–05–25] Retrieved from the Internet:<URL.www.healinx.com>.

MedicalLogic, 1999 [retrieved on 2000–05–24] Retrieved from the Internet: <URL:www.medicallogic.com>.

SaluHub, 1999 [retrieved on 2000–05–24] Retrieved from the Internet: <URL:www.salu.net>.

* cited by examiner

ELECTRONIC PROVIDER— PATIENT INTERFACE SYSTEM

FIELD OF THE INVENTION

The present invention relates, in general, to an automated system of electronic communications between a health-care or medical service provider and his/her patient, for the purpose of providing a simple, reliable and effective interface for rapidly exchanging inquiries, responses, data, services and information between the both parties for the mutual benefit and satisfaction of each.

BACKGROUND OF THE INVENTION

Health care used to be simple and reliable. When symptoms of an illness appeared, either the doctor visited the patient's home or the patient went to the doctor's office. But such services no longer exist. Home care by doctors stopped decades ago, and even visits to the doctor's office or hospital must now be preceded by authorization from a managed health care provider. Under certain conditions, care may now be refused entirely unless payment is made in advance. Consequently, consumers have, by necessity, become more active in managing their own health, and they worry about how much they must spend on health-care services.

Meanwhile, health-care providers are now under more pressure than ever to treat a greater number of patients in the same amount of time, but with diminishing resources. The pressure began in the 1980's with the advent of managed health care and the associated reduction in physician compensation in the face of an inflated economy. This trend continued through the 1990's, but was exacerbated by patient demands for an increased voice in their care, better access to the doctor and more information about their medical situation. As a result of cost cutting, merging and reengineering, doctors have been left with the dilemma of either reducing service to their patients or increasing capacity. The effect has been a mutual disenfranchisement of both doctors and patients. This is evidenced by the increasing number of doctors, who are now leaving medicine to pursue other careers, and by the fact that the ones remaining are considering resorting to labor unions to protect their interests.

A number of commercial entities have attempted to assist doctors by creating "back-office" operations and management solutions. Back office solutions are defined as those processes applied to the current day-to-day management of a doctor's practice (i.e., eligibility, claims, on-line practice management, etc.). However, they do not address the doctor's relationship with the patient. Unfortunately, implementation of a back-office service has a high impact on the practice, because it requires a significant addition of resources and necessitates system and process modifications in the doctor's office, including substantial training of staff, integration and work process changes. Therefore, the back-office approach is tied to what have proven to be insurmountable problems involving additional time, cost and management expenditures for the practice.

Companies that sell in-house systems for the back-office space, include medical record vendors, such as Medicalogic and Epic, as well as practice office management vendors (POMS), such as IDX. Recently, such vendors have been redeveloping their burdensome back-office solutions to deliver them on-line and compete in the space currently occupied by Healtheon/WebMD. Nevertheless, whether delivered on-line or in-house, each of these solutions has a high impact on the operation of the doctor's office, and as a result will face significant hurdles before they can be adopted regardless of cost, delivery method or the like.

At the same time we now live in an age of information and technology. The Internet provides a number of services to its users, including the World Wide Web (WWW), which is essentially a collection of files, often referred to as Web pages, in a variety of formats stored on host computers, often called Web servers. A collection of Web pages published by an organization is typically termed a Web site, wherein its first or highest level page is termed a "homepage." Consequently, Internet technology has spawned a healthcare industry online to provide health-care information to both patients and professionals, and for any number of reasons, individuals are turning to the Internet with increasing frequency for expertise regarding diseases, medicines, treatments, alternative health products, and even the selection of doctors.

To provide greater access to the Internet the communication protocols and languages utilized by users and servers have become standardized. These protocols include (i) the Hyper-Text Transfer Protocol (HTTP), which is an application-level protocol for distributed, collaborative, hypermedia information systems, and the communication protocol used for communications between users and servers, and (ii) the Transfer Control Protocol/Internet Protocol (TCP/IP), wherein the TCP portion is the standard Internet transport specific protocol (or set of protocols) for communication and data exchange between computers or applications. TCP/IP handles issues such as packetization, packet addressing, handshaking and error correction. Also standardized is the language in which users (the patient or consumer seeking information) and servers (the information service providers) communicate, which is called the Hyper-Text Markup Language (HTML).

Although most Web pages are textual documents described in HTML, the pages may also include images, still or moving, and audio data. The key feature of HTML is the ability to define Hypertext Links within the document, which provide access points to other parts of the same document, other Web pages or other Internet facilities.

To access the World Wide Web, the user employs software on his/her computer known as a Web "browser." Commercially available browsers include, for example, Netscape Navigator™ and Microsoft Internet Explorer™. The browser provides an interface, a local cache, and a set of processes for accessing the Internet, navigating over the myriad sites, communicating with a selected site, including E-mail, error detection and correction, and security facilities.

HTTP messages consist of either requests from user to server or responses from server to user. The user enters the address (Uniform Resource Locator (URL)) of a Web page into his/her browser, or selects one from a list of previously stored addresses, often referred to as Bookmarks. The URL is a descriptor that specifically defines a type of Internet resource and its location, i.e., the address of the Web server holding that Web page, which has an address beginning "HTTP://". Access to most Web pages is unrestricted; however, it is possible for access to be controlled by the use of passwords and security restrictions After the Web page address is entered, the Web browser automatically contacts the user's service provider, dialing up a link over the telephone network if necessary, and issues a request for that Web page. The Web browser then sends an HTTP request to the Web server, which responds to the HTTP request by sending the requested HTTP object to the user. In most cases, the HTTP object is a plain text (ASCII) document that is written in HTML language, which the Web browser displays on the user's computer screen. The HTML document contains all of the information needed by the browser for displaying a Web page on the user's computer. Typically, the document contains "hyperlinks" that the user can click; doing so causes the Web browser to send a request to the Web server for one or more additional documents. The part of the link displayed to the user is generally distinguished from other parts of the page, for example text may be underlined or in a different color.

Generally the user's computer relies upon a mouse (or trackball) and an on-screen pointer for inputting commands. For example, the pointer is often arranged to change shape or color when located over a hypertext link. When the user selects a hypertext link, usually by positioning the pointer over it and clicking a mouse button, the Web Browser software automatically accesses the corresponding Web page.

The Web browser also evaluates the HTML data to determine if there are any embedded hyper-link statements, which would require subsequent browser requests, which would then be initiated by the browser. The functions of browsers and server software, examples of HTML-coded documents, and the use of links and similar HTTP protocol constructs are described by, e.g., Judson, U.S. Pat. No. 5,572,643, issued in 1996.

Thus, the Internet has become a convenient and powerful tool for many consumers seeking information about a variety of topics, including healthcare, particularly as it becomes increasingly difficult to get service from medical personnel. However, reliance on the Internet for such crucial information could prove hazardous to a patient's health. While there are many legitimate and valuable consumer health portals and health-care sites on-line, such as drKoop.com, Intellihealth.com and AmericasDoctor.com, as well as those by recognized groups, such as the American Diabetes Association, medical professionals, government officials and consumer advocates have recently expressed grave concerns that information from such reputable sites might be misunderstood by consumers. Moreover, less than reputable sites exist that have misled patients by making deceptive claims of miracle cures and bogus breakthroughs.

Patients have, however, expressed concerns and reservations because the information on the Internet is not delivered from "a trusted source," so that even after hours of searching, the patient may not be sure that he has gotten the "right" information. Given the option, patients still consider their personal physician to be the most reliable source of health-care information. Consequently, it is not unusual for the patient to collect a wealth of information from the Internet, and then take it to his/her doctor for validation, which either the doctor will refuse to do, or which will exacerbate the doctor's ever increasing time constraints. Therefore, even in this age of information there remains a significant need for effective and reliable communication between patients and their doctors, so that (i) the patient is not left to rely on information of unknown accuracy from arbitrary service providers on the Internet, (ii) trust in medical practitioners and service to the patient can be restored, and (iii) billing, scheduling and administrative functions are efficiently facilitated for both parties. Moreover, there remains a need in society for restoring communications between doctors and their patients, for enhancing service to patients, and for expanding the capacity of the medical practice, without additional work by the doctor or his/her staff.

SUMMARY OF THE INVENTION

Recognizing the endemic and chronic lack of adequate communication between health-care providers and their patients, the present invention provides a communication system for providing automated, electronic communications between at least one health-care provider and a plurality of users of the health-care provider, wherein the communications occur over a communications network through a provider/patient interface, said system comprising:

a central server, comprising one server or a logical unit of multiple servers;

a provider's service computer, a plurality of users' computers; and a communication network for enabling communication between and among the central server, the provider's service computer, and the plurality of users' computers.

In a preferred embodiment, the communication system of the present invention is the first Electronic Provider-Patient Interface (the ePPi™). The preferred users of the ePPi system are patients, and the preferred provider is the patient's own doctor or health-care practitioner ("the practice").

The ePPi system addresses one of the patient's primary concerns—access to information and services from their own doctor. The ePPi system, provides an automated service to patients, through which access to their own doctor is provided over the Internet without additional work for the doctor's office because it is based upon existing records. Prior to this invention, patients were frustrated by their inability to gain access to their doctors, while doctors were equally frustrated because there simply was not enough time for them to provide the service they would have liked to their patients. Health-care providers realized that they had to find a way to increase capacity without sacrificing quality, service or patient access; but without increasing cost. The ePPi system offers an automated and efficient provider-patient communication system that resolves both the patient's and the provider's aggravation by providing appropriate health-care information and services.

At the core of the present invention is a fully automated mechanism for generating a personalized area (patient pages) for each patient within the doctor's or health-care group's Web site in the ePPi system. Custom mappings are established in the ePPi system between the practice's common visit codes, diagnoses codes and procedure codes, thereby permitting automatic delivery of content to the patient through the logic of the system. Thus, the patient's page is created without extra work or effort by the practice through an automated process that uses the data that has already been entered into the practitioner's scheduling and billing systems. As a result, once the patient has logged into his/her own Web page, he/she can also access a variety of practice-based services including, appointment requests and updates, prescription refills, online triage, health search information and the like.

Based upon the previously entered content from the practice about the patient, and the coded information added to the system following each additional visit, diagnosis or procedure in the patient's history (all of which contribute to determining the content of the patient's page), visit-specific content is made available on-line to the patient after a visit to the practice. This offers the patient significantly more information than he/she could have absorbed during a typical visit with the physician. Patient inquiries or requests regarding episodic events, such as appointment and prescription refill requests, can be submitted at the convenience of the patient, and can then be handled by the doctor's staff much more efficiently; both in terms of time and flexibility, than ever before possible.

Moreover, the ePPi system is a powerful patient relationship management tool in the doctor's front-office practice. Patients can become increasingly involved in their own care, and less dependent on physician office resources. For the medical practice, this translates into reduced cost, increased capacity and increased customer satisfaction. For the patients, the effect is not only enhanced savings and satisfaction, but the on-line information is now available from their own doctors, rather than from unreliable sources on the Internet. In addition, the system captures unique data that is of significant interest to researchers and suppliers of health-care products, which can be utilized to affect patient behavior (e.g., compliance), product development and marketing, on-line sales and advertisement.

The ePPi implementation collectively embodies a set of one or more server computers, which perform various tasks. These computers may or may not necessarily be co-located in a single facility. Regardless of their physical location, they comprise a logical unit, working in concert to provide the ePPi functionality. The functional components provided in the communication system of the present invention include:

a Web server capable of responding to HTTP requests from users by sending HTML formatted documents to those users;

a database server capable of maintaining complex relationships between practices, patients, doctors, and healthcare informational content;

a modular data collection program that receives information from doctors' or practitioners' scheduling and billing systems regarding patient visits, in a variety of different data and file formats, reformats the information, and stores it in the database;

an electronic mailing capability which supports the automated transmission of notifications to patients when new information is added to the database, as well as the transmission of notifications to practice-designated personnel whenever new requests from patients are made (e.g., appointment scheduling requests, prescription renewal requests, non-urgent questions for a doctor, etc.).

The communication system of the present invention provides a system, wherein there are one or more providers, each of which is in communication with a plurality of users. Additional component servers can be added to the system as new functionality is introduced or additional capacity is needed. Furthermore, the architecture has been designed with maximum flexibility in mind, so that the ePPi Service Center may be scaled appropriately to the needs of the users. Thus, it may be required to have more Web servers and fewer database servers, or more database servers and fewer Web servers. A single computer could host only one functional component, or a combination.

As the system and database are updated, refined or modified, additional features will be introduced. For example, the present invention further offers the ability to evaluate prescribed medications, in the event that a particular drug is not available, or that an equivalent generic drug may cost substantially less. Nevertheless, the system will remain unique to each individual client since criteria that are of interest to one patient may be of no interest to another. In the preferred embodiment of the present invention, the server uses a hypertext transfer protocol ("HTTP") to communicate over the network with either providers or users; such providers and users also communicate with the server using the hypertext transfer protocol. The server typically includes at least one server processor, a memory and a computer readable medium, such as a magnetic ("hard disk") or optical mass storage device, and the computer readable medium of the server contains computer program instructions for transmitting the file from the server system to the providers" or user's system and for transmitting static or dynamic objects to the provider's or user's system, respectively. The provider or user typically will utilize a processor and a memory and a computer readable medium, such as a magnetic or optical mass storage device, and the computer readable medium of the provider or user contains the computer program instructions for receiving and storing static, dynamic or mixed objects at the provider's or user's computer. The static object, in a typical embodiment, will include a name attribute, such as a domain attribute.

The present invention further provides a communication system, wherein the communication network is either an Internet or intranet network. The preferred communication network is the Internet.

The preferred communication system of the present invention comprises a provider-patient interface Service Center, wherein custom content is dynamically assembled and delivered. Moreover, delivery in the preferred system occurs over the World Wide Web, and custom content is preferably assembled using Active Server Pages (ASP) technology. Custom content is preferably selected from a library of information, and the selection is based upon specific data received from the provider about each user, who is served by the provider. The data about each user comprises information about each user's visits to the provider. Further, the custom content selection in the preferred communications system is based upon logical mappings that reside in the relational database server.

The present invention also provides a communication system comprising a unique provider's Web site for each of the one or more providers, wherein each Web site is supported by or in communication with the central server through the Service Center. Moreover in the preferred communication system, the provider/patient interface provides a fully automated mechanism for generating a personalized page or area within the provider's Web site for each user serviced by the one or more providers, and the provider's Web site is in communication with at least one user's computer through the provider/patient interface. In certain preferred embodiments of the communication system, at least one provider's Web site and at least one user's computer are hyperlinked through the provider/patient interface.

In the preferred communication system of the present invention computer system, submissions of information from one or more providers and from the users of the electronic communications system are in standardized formats. Moreover, the standardized formats are preferably derived from standard administrative and billing codes used by the provider.

The present invention further provides a method of automatically and electronically communicating between at least one health-care provider and a plurality of users serviced by the health-care provider, wherein the communication occurs over an electronic communication network through a provider/patient interface, wherein the method comprises (i) a communication is initiated from one of the plurality of users to his/her provider for information; (ii) the communication is transported through the provider/patient interface over an electronic communication network to a site which is unique to the provider on a central server; whereupon the communication is automatically reformatted and processed or stored; (iii) the communication is electronically compared with mapped content, which has been previously provided by the practice to the central server, to formulate a response as a static or dynamic object, or a combined static and dynamic object; and (iv) the communication is automatically returned, along with the requested information, to the user's computer, whereupon the communication and information are read by the user or stored on the user's computer. Moreover, when the user's communication includes a communication or inquiry regarding additional information or an episodic event, the method further comprises the additional step of notifying the provider and the user automatically that a response or information has been sent to the user's computer.

The preferred embodiment of the method of the present invention is implemented by the electronic provider-patient interface system (the "ePPi system").

In the method of the present invention, the central server comprises: a Web server capable of responding to HTTP requests; a database server capable of maintaining complex relationships between users and information content; and a modular data collection program capable of receiving information as coded data from practices in a variety of different formats, and reformatting and storing the information. The central server may further comprise an electronic mailing capability to support the automated transmission of notifications to users or providers.

In addition, in the method of the present invention, there are one or more providers, each of which is in communication with a plurality of users.

In the method of the present invention, the communication network is either an Internet or intranet network. The preferred communication network is the Internet.

The preferred method of the present invention comprises a provider-patient interface Service Center, wherein custom content is dynamically assembled and delivered. Moreover, delivery in the preferred method occurs over the World Wide Web, and custom content is assembled using Active Server Pages (ASP) technology. Custom content is preferably selected from a library of information, and the selection is based upon specific data received from the provider about each user, who is served by the provider. The data about each user comprises information about each user's visits to the provider. Further, the custom content selection in the preferred method is based upon logical mappings that reside in the relational database server.

The present invention also provides a method comprising a unique provider's Web site for each of the one or more providers, wherein each Web site is supported by or in communication with the central server through the Service Center. Moreover, in the preferred method the provider/patient interface provides a fully automated mechanism for generating a personalized page or area within the provider's Web site for each user serviced by the one or more providers, and the provider's Web site is in communication with at least one user's computer through the provider/patient interface. Also, in certain preferred embodiments of the method, at least one provider's Web site and at least one user's computer are hyperlinked through the provider/patient interface.

In the preferred method of the present invention computer system, submissions of information from one or more providers and from the users of the electronic communications system are in standardized formats. Moreover, the standardized formats are preferably derived from standard administrative and billing codes used by the provider. The information delivery by the preferred method is in HTML format.

In yet another preferred method of the present invention automatic and electronic communication is made possible between and among at least one health-care provider and a plurality of users serviced by the health-care provider, wherein the communication occurs over an electronic communication network through a provider/patient interface. The method comprises the following steps: (i) a notification or communication is initiated from a provider to one of the plurality of users serviced by that provider; (ii) the notification or communication is transported through the provider/patient interface over an electronic communication network to a site which is unique to the provider on a central server, whereupon the notification or communication is automatically reformatted and processed or stored; (iii) the notification or communication is electronically compared with mapped content, which has been previously provided by the practice to the central server, to automatically formulate the notification or communication to include such additional objects or information as may be assigned by the mapped content; (iv) the notification or communication is automatically forwarded to the user's computer, whereupon the notification or communication is read by the user or stored on the user's computer; and (v) the provider and the user are both automatically notified that the notification or communication has been sent to the user's computer.

One embodiment of the present invention provides an on-line appointment system. A user can browse the information provided by the provider's Web site on the central server, preferably on his/her own patient page. The user can then request information, such as an appointment for a selected time and date, and for a particular doctor in the practice. The server then sends static information related to the appointment to the browser on the user's computer for storage, along with automatic notification to the provider and the user that information has been sent. When the user wants to confirm the appointment, the browser sends the corresponding static information to the practitioner's specified Web page for processing.

Another embodiment of the present invention provides an on-line information service, wherein information regarding a variety of topics, such as a particular symptom or disease, is provided either in response to an inquiry from the user or as available data in the provider's site on the Web server. The user may browse through the various pieces or types of information by making HTTP requests from the provider's Web site on the central server. As stated above, the patient has the security of knowing that the information is accurate since it is provided on-line by his/her own doctor, rather than from an arbitrary and unknown source on the Internet.

These and other features of the present invention will be disclosed in the following description of the invention together with the accompanying figures.

BRIEF DESCRIPTION OF THE FIGURES

FIG. 11 is a conceptual diagram depicting the objects and application of a generic Plug-In.

DESCRIPTION OF THE INVENTION

Figure 1:
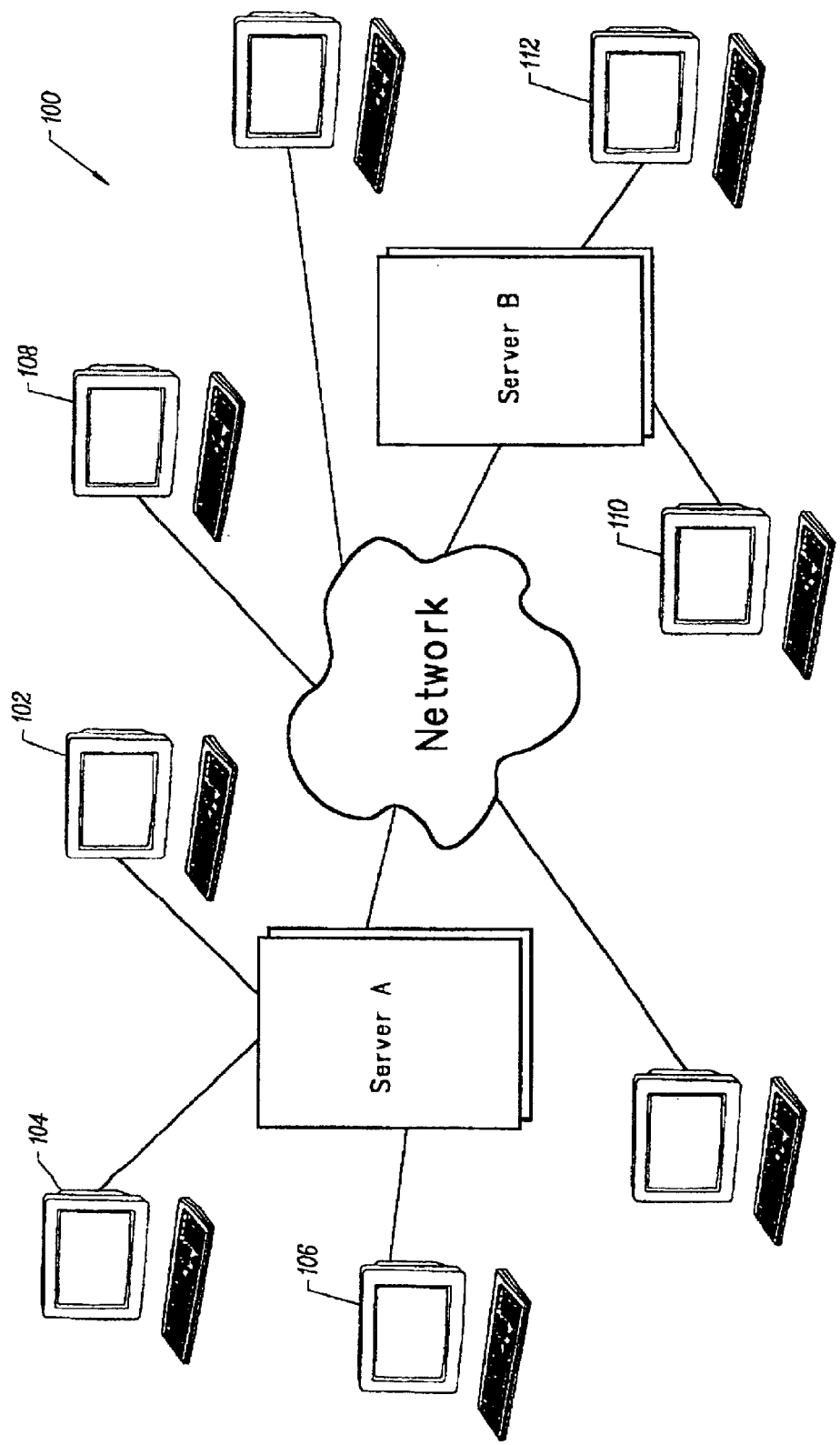
FIG. 1 is a conceptual diagram of a computer network such as the Internet and the general client/server model.

The Electronic Provider-Patient Interface (ePPi™) automated communications system creates and delivers personalized patient pages, service and information, thereby permitting doctors to provide personalized service to their patients with little or no additional effort. Reduced costs and increased capacity are achieved by the ePPi system because there are far fewer calls to the doctor or staff for simple inquiries and follow-up instructions, for prescription refill and appointment requests, and for directions to the office, laboratory, radiologist or specialist's office, general information and the like. More efficient work processes can be established by managing call backs, as opposed to reacting to interruptions by call-ins. Information is more effectively handled under the ePPi system because the information is gathered and reviewed in advance. In addition, by means of the present invention, more accuracy can be achieved on computerized forms, and there is improved patient compliance.

For both the patients and the doctors, the ePPi system is considerably more reliable and effective than commercial or arbitrary Internet health-care portals. In fact, patient feedback and usage statistics from those who have tested the ePPi system validates that patients much prefer this approach. Patients have indicated that they value the fact that the health-care information is delivered to them from a source they can trust, and without the need to search to find it. Doctors have indicated that they prefer the ePPi system because although fully automated, they are familiar with the content, know how the patient got the information, and can control whether or not advertisers have access to the patient.

In separate test studies patient satisfaction was seen to have improved when the ePPi system was used because patients are provided access to the services of the practice 24 hours a day, 7 days of the week. Patients can confirm what they thought they understood during their patient visit, and in addition receive more information than they could have absorbed at the visit. The effect is that-the-patient feels more informed, more involved and better served. Patients value the personalized services offered by the practice using ePPi, and as a result, trust in the doctor is increased. Patients also appreciate the flexibility and privacy afforded by the ePPi system in retrieving information from the practice. Because the patient page is on the ePPi system, the patient spends far less time filling out forms on a clipboard at the doctor's office, and they receive much more personalized answers to questions. Finally, neither party needs to track-down or wait for the other by telephone. Therefore, the patient can make inquiries and receive replies and information without having to wait by the telephone.

The ePPi system and methods for maintaining static information in a client-server based computer network system are disclosed. The following description is presented to enable any person skilled in the art to make and use the invention. However, it will be apparent to one skilled in the art that these specific details are not required to practice the present invention. Although, strategic partnerships with doctors and medical care practice groups are essential to the operation of the ePPi system, eventually, the system can be distributed to, for example, schools or case management companies.

The ePPi system is focussed at the physician's front office, and depends upon the need for doctor/patient communications. Thus, the system fulfills a different need than that which is provided by companies, such as Healtheon/ WebMD, which primarily focus on back office services. By comparison, the ePPi patient/provider system is an extremely low impact solution for the physician's front office, which allows large numbers of practices to quickly offer a better conduit to information and health-care than a back-office solution. By a "front office" solution is meant one that affects the direct communication between a patient and the doctor, i.e., in person, by telephone, by hand-outs, and the like. The enhanced communication provided by ePPi involves little or no training, no conversion of existing systems, and is based essentially entirely on the doctor's own existing administrative systems.

There are presently no competitors in this type of front-office management, and no system comparable to the ePPi system exists for providing automated doctor/patient communication on-line. Nevertheless, as the commercialization of the present invention is developed, and the success of the ePPi system is recognized, others will undoubtedly try to duplicate the ePPi system, although it may be called by a different name, and it may include one or more additional services. Vendors with significant market shares of the practice office management software (POMS) would have a substantial market advantage if they were to offer a competitive product based upon the ePPi system.

Therefore the following descriptions of the ePPi system and selected specific applications of the system are provided only as examples. Various modifications to the preferred embodiments will be readily apparent to those skilled in the art, and the general principles defined herein may be applied to other embodiments and applications without departing from the spirit and scope of the invention. Thus, the present invention is not intended to be limited to the embodiments shown, but is to be accorded the widest scope consistent with the principles and features disclosed herein.

I. General Implementation of a Client-Server System on the Internet

Once understood, the many terms and general principles involved in client-server computing, as shown in FIG. 1 and described below, will be used to generally characterize and describe the ePPi system. FIG. 1 illustrates a conceptual diagram of a computer network (100), such as the Internet Computer Network (100), which comprises small computers (such as computers 102, 104, 106, 108, 110 and 112) and large computers, such as computers A and B, commonly used as servers. In general, small computers are "personal computers" or workstations and are the sites at which a human user, such as a patient, operates the computer to make requests for data from other computers or servers on the network. Usually, the requested data resides in large computers.

In the present scenario, small computers are clients and the large computers are servers. Notably, in the present specification, the terms "client" and "server" are used to refer to a computer's general role as a requester of data (the client, representing in the present invention, e.g., the patient) or provider of data (the server, representing in the present invention, e.g., the ePPi system acting on behalf of the provider or practice).

Although the HTML and other elements are envisioned as located on a remote server, it is also possible that some or all of these may have been loaded into a storage cache during a previous request during this or a previous session without departing from the spirit of the invention. A client can refer to any device connected to the ePPi system via the Internet or other IP (Internet Protocol) transport methods, including, but not limited to, devices such as televisions, computers, hand-held or wireless electronic devices, or any device that uses IPs and a transport medium. Moreover, the networking communication lines as implemented can be broadly construed to include, without limitation, any method or link known in the art for transferring data to and from a server including telephone wires, coaxial or fiber cable, radio waves, infrared radiation ATM link, FDDI link, satellite link, cable, twisted pair fiber-optic broadcast wireless network, the Internet, the World Wide Web, or even a Local Area Network (LAN), Wide Area Network (WAN), or any other intranet environment, such as a standard Ethernet link. When alternative transport methods are used, the client communicates with the system using protocols appropriate for the network being used. All such embodiments and equivalents are intended to be within the scope of the present invention.

In general, the size of a computer and the resources associated with it, do not preclude the computer's ability to act as a client or a server. Further, each computer may request data in one transaction and provide data in another transaction, thus changing the computer's role from client to server, or vice versa. The distance between servers or between client and server(s) may be very long, e.g., across continents, or very short, e.g., within the same city. Further, in traversing the network the data may be transferred through several intermediate servers and many routing devices, such as bridges and routers.

The World-Wide-Web (the "Web") uses the client-server model to communicate information between clients and servers. Web servers are coupled to the Internet and respond to document requests from Web clients through their browser programs.

In operation, a plurality of provider or patient processors opportunistically couple one or more of a plurality of HTML document servers in the ePPi Service Center. It should be appreciated that each patient and the one or more servers comprising the ePPi Service Center can establish and maintain concurrent "sessions" or dialogs with a plurality of the opposite number. That is, as in FIG. 1, client 1 could interact with servers A and B, while client 2 could be in session with servers B and C.

The ePPi system inter-operates with standard Web server and database components to mediate and enhance communication between a patient and his/her doctor's office. The patient receives e-mail notifications from the ePPi Service Center, automatically delivered directly to his/her own e-mail service provider and which are accessible using his/her current e-mail software. To access the personalized information on the doctor's Web site (hosted on a Web server at the ePPi Service Center), the patient uses a standard Web browser program on his/her PC, Web-TV device, wireless hand-held device, or the like. Nevertheless, there is still some latitude in choosing the basic platform on which the ePPi is constructed. For example, the following software components comprise the preferred ePPi platform:

- a base operating system for the computer(s) that provide the ePPi functionality;
- a Web server program to respond to HTTP requests from a user's Web browser, and deliver HTML or other documents for display on the user's computer screen;
- a Database Management System to store the information about the practices (including site branding options), patients (including visit-specific data), and third party informational content (patient instructions, healthcare articles, etc.), and
- a set of development tools and languages with which the unique functionality and features of the ePPi system are constructed.

The inventors have chosen to implement the ePPi system using the following components:

- The Windows NT Server operating system. Windows NT™ is a multi-platform operating system provided by Microsoft Corp. of Redmond, Wash., capable of utilizing full-power, dual-processor computer systems. A security infrastructure is totally integrated with Windows NT Server, enabling an easily maintained and highly secure Web development and deployment environment.
- The Internet Information Server (IIS) Web server, and the Site Server program (both from Microsoft). The Windows NT server includes IIS, which is a completely integrated Internet application platform, including a high performance Web server, an application development environment, integrated full-text searching capability, multimedia streaming, and site management tools. Site Server provides advanced capabilities for content management and publishing, mail-merge, and personalization.
- The Microsoft SQL Server database management system. Also from Microsoft Corp. of Redmond, Wash., SQL Server is a fully relational database management system (RDBMS) that can support the complex data relationships that are central to the ePPi system's personalization of content to each patient based on their encounters with his/her doctor.
- Microsoft's Active Server Pages technology (included in IIS), with VBscript and JavaScript programming languages providing logic to assemble dynamic HTML pages, and development tools that include FrontPage, Visual InterDev, and Visual SourceSafe. All of these development tools are also from Microsoft Corp. of Redmond, Wash., and they offer a high degree of inter-operability. However, no single tool is necessarily a requirement for the chosen implementation, and one reasonably skilled in the art can develop equivalent functionality using similar tools from different suppliers.

Nevertheless, the ePPI system need not be, and is not intended to be limited to use on Windows NT operating system, and the presently provided description is provided only as representative and exemplary information. One of ordinary skill in the art would know, based upon the present disclosure that many equivalent procedures, components and tools are available that function in substantially the same way, to achieve substantially the same results as those which are described and can be substituted so long as the ePPi system continues to function in substantially the manner herein disclosed. For example, the base operating system could be UNIX (or Linux), the Web server could be Netscape, the database server could be Oracle, and the development tools could include CGI, Pert, Java, TCL, and the like. All such embodiments and equivalents are intended to be within the scope of the present invention.

As an example, the following sequence describes a representative scenario demonstrating the ePPi enhanced provider-patient interaction and how it interacts with the practice scheduling and billing systems, with a patient, and with the practice staff. The ePPi provides a number of enhanced communication pathways between the provider and the patient.

1. A patient (example: Jane Doe) requests an appointment, either by phone or using an on-line form on the ePPi practice Web site.

2. One of the practice's schedulers books the appointment, using the practice's normal scheduling software.

3. The practice transmits a data file from its scheduling system to the ePPi Service Center, where it is loaded into the database. One of the records in the datafile reflects patient Jane Doe's newly scheduled appointment. Using mappings that were set up in the ePPi database for this specific practice, the ePPi Service Center associates Jane's new appointment with specific patient instructions that are uniquely relevant to the reason for Jane's visit.

4. The ePPi automatically sends an e-mail message to Jane Doe, informing her that there is new information for her at the practice's Web site. Upon receipt of the e-mail notification, Jane Doe clicks onto the practice Web site URL at the bottom of the e-mail address (or types the URL into her Web browser program, if her mail software does not support the ability to click on a URL). Thus, standard operating Internet communications are enhanced by the ePPi's database of patient-specific information and practice-specific branding options 5. The ePPi Service Center responds to the Web browser on Jane Doe's computer by transmitting an HTML page to Jane's Web browser, which contains the "home page" contents for Jane's doctor's office, with the branded display options defined specifically for the practice's Web site.

6. Jane Doe sees the practice Web site home page on her browser. She clicks the hyperlink to display the site's secure Login form, types her user name and password, and clicks the form's "Submit" button to transmit her login information in a secure manner to the Web server in the ePPI Service Center.

7. The ePPi Web server receives Jane Doe's login information and validates her in the ePPi database. Once her identity has been authenticated, the ePPi Web server dynamically assembles an HTML page that contains information about the practice, as well as information specific to Jane's own recent and upcoming scheduled visits, and transmits this personalized home page to Jane's Web browser.

8. If Jane clicks a link on her personalized home page to request more detailed information about her new scheduled visit, the ePPi Web server retrieves details from the ePPi database about Jane's new visit (the date/time, the doctor's name, and the reason for the visit), dynamically assembles the information into an HTML page that is formatted with the branding options for Jane's doctor's Web site, and transmits the page to Jane's Web browser. The page includes a hyperlink that Jane can click for more detailed information and instructions about her upcoming visit.

9. If Jane clicks the hyperlink to read the personalized instructions, the ePPi Web server retrieves the visit-specific instructions related to Jane's upcoming appointment from the database, formats the information according to the branding options,for the practice Web site, and transmits the HTML page to Jane's Web browser.

10. Jane visits her doctor on the scheduled date and time of her appointment. During the visit, the doctor or nurse who sees Jane records information on a charge sheet that indicates the procedure(s) performed, and the diagnosis(es) observed.

11. After Jane's visit, one of the practice's billing clerks enters the diagnosis and procedure information into the practice's normal billing software. The diagnoses and procedures are entered using healthcare industry standard ICD-9 and CPT-4 codes, which facilitate collection from insurance companies and other third-party payers.

12. The practice transmits a data file from its billing system to the ePPi Service Center, where it is loaded into the database. One of the records in the datafile contains the diagnosis and procedure codes for Jane Doe's recent visit. Using mappings that were set up in the ePPi database for this specific practice, the ePPi Service Center associates Jane's own diagnoses, and the procedures which were performed during her visit, with specific post-visit instructions.

13. The ePPi automatically sends an e-mail message to Jane Doe, informing her that there is new information for her at the practice's Web site.

14. Upon receipt of the e-mail notification, Jane Doe clicks on the practice Web site URL at the bottom of the e-mail address (or types the URL into her Web browser program, if her mail software does not support the ability to click on a URL). She enters her unique user name and password using the secure Login form, and sees her personalized home page, which now includes a notification that there are new instructions and recommended reading from her doctor's office.

15. Once Jane clicks the link, the ePPi Web server reads the ePPi database to determine the latest patient instructions, articles, recommended reading, etc. that are relevant to Jane, based on her own diagnoses and procedures. The ePPi Web server dynamically assembles this information into an HTML page, brands it with the options for the practice Web site, and transmits the page to Jane's Web browser.

16. Jane reviews the list of instructions and articles. To read a particular item in full, she clicks on the title of the item. In response, the ePPi Web server formats the information according to the branding options for the practice Web site, and transmits the HTML page to Jane's Web browser.

The foregoing scenario is, of course, intended only to be representative of some of the features of the ePPi system. It is not meant to depict all of the capabilities of the ePPi system, nor limit same. However, the scenario was specifically chosen to illustrate how the ePPi system uniquely maps data from the practice scheduling and billing systems, into information libraries, in order to deliver highly relevant content to patients based on their interaction with their doctor's office.

II. Characterization of the ePPi System

For the purposes of the present invention certain terms are defined. The terms "doctor," "physician," "health-care provider," and "practitioner" are used interchangeably with the term "provider" to refer to the individual, service or practice, which is registered and authorized by the ePPi system, and on whose behalf the ePPi system presents to the patient a "branded" Web site. For example, the term "provider" is used in the name of the electronic provider-patient system, but it is intended to generically refer to one or more doctors, health care service providers or practitioners, or the like, registered in the system, as would be understood by one of ordinary skill in the art. It could refer to a single doctor, to an office of doctors, to a group of doctors working out of more than one office, to a hospital group or medical center, to a group of small hospitals, or to any variation thereof.

The term "provider" could refer not only to medical doctors, but also to dentists, opticians, physical therapists and the like, alone or in combination with physicians. The service could be extended to alternative medical practices, such as chiropractors, herbalists, acupuncturists, aroma therapists, and the like. Moreover, it could eventually include veterinary practices, schools, case managers and the like. Broadly, whether an individual office or a group, the service provider, including the medical and administrative staff, regardless of the specialty, is referred to as a "practice."

The term "patient" is used interchangeably with "user," "client," or "consumer" and refers to the authorized individual receiving the service or information, and operating the client computer. Thus, the "patient" may in a broad sense refer to the patient's representative, such as a parent acting on behalf of their child, when the child is the actual patient of the doctor. In the alternative, if the service is used for veterinary offices the term "patient" broadly refers to an owner, trainer or care-giver representing the animal which is actually being treated. As described below, authorization is required from the practice, which is registered on the ePPi system, before a patient is added to the system.

Of course, because the patient services are individualized, a single patient could participate in more than one member practice using the ePPi system. Each would manage its own patient page and provide specific patient information, which need not, and presumably would not, be the same from each practice.

Although based upon the general principles described for client-server interactions, several factors at the core of the ePPi system make it unique.

1) Context—Information from "My Own Doctor"

The ePPi system delivers all information within the context of services offered by the patient's own physician. For example, a message from a child's pediatrician (which is automatically generated) that it is time to get a vaccination is just a mouse click away from an on-line appointment request with the same doctor. Within the same view, the parent (or patient in the case of other specialties) has access to a number of related services, including, for example, but without limitation, a personalized list of medications with related information, prescription refill request, pre- and post-visit instructions, practice news, provider directories and much more.

All information is displayed in the patient's personal page (whether it is a personalized instruction or the result of a search) and comes through his/her own physician's Web service. Consequently, for the patient, all concerns are alleviated about the value or validity of the information they have received.

2) Coordination—More Than Just Integration

By leveraging data from existing practice systems and putting it in a context that makes sense to the patient, the ePPi system provides a service that is highly valuable to the patient, but which requires little or no additional effort for either the physician or his/her office staff. The system does much more than simply integrate data from disparate systems into a single view for the patient, the ePPi system coordinates data from those systems to actually decide what other information should be delivered to the patient.

For example, based on a procedure or the patient's type of office visit, which is stored in the doctor's office management system, the ePPi delivers to the patient's own personal page, a specific instruction set located in an on-line self-care guide. However, this is but one example of how the ePPi leverages and coordinates information stored in multiple systems to create a specialized set of data to enhance the patient's access and understanding of his/her medical care. There are many, many such applications, which are all processed automatically that provide equally valuable increased service to the patient, without increased cost or effort to the medical staff.

3) Simplicity

Testing has proven that a new practice can implement the ePPi system with just a few hours of initial start-up time for the office staff, and with minimal effort thereafter. Training consists of a simple tutorial, without the need for software specialists or training personnel, and takes only 30 minutes to complete.

To facilitate a low cost and low impact implementation of the ePPi system at the doctor's office, a solid architectural foundation has been put in place to permit new sites to be rapidly and efficiently brought on-line.

4) Configurability

The "look and feel" of the Web site is uniquely configurable for each practice. Accordingly, each practice has a distinct, branded Web site. Colors, fonts, logos and incidental graphics are matched to the practice's existing or newly chosen design theme. Each practice can, therefore, choose from the pre-defined set of available functionalities (e.g., appointment requests, medical lists, etc.) with the ability to extend the core features with customized Web pages, forms, and service requests that are tailored to the style and established protocols of the particular practice.

5) Scalability

The ePPi system has been built to handle the increasing volume of Web pages, database content, and I/O processing that will be involved as increasing numbers of practices are brought on-line. The ePPi core architecture achieves both configurability and scalability by combining industry standard non-proprietary components in a unique way that takes into account the thousands of possible relationships that could possibly occur among patients, providers, staff, conditions, discrete data elements and the like, to produce a proprietary architecture that allows for low impact, rapid implementation and flexibility.

The forementioned five characteristics—Context, Coordination, Simplicity, Configurability, and Scalability—are realized through the ePPi's functional architecture. These characteristics also distinguish the features, attributes and elements of the ePPi system from existing or potential other front-office communication solutions, if any.

Figure 2:
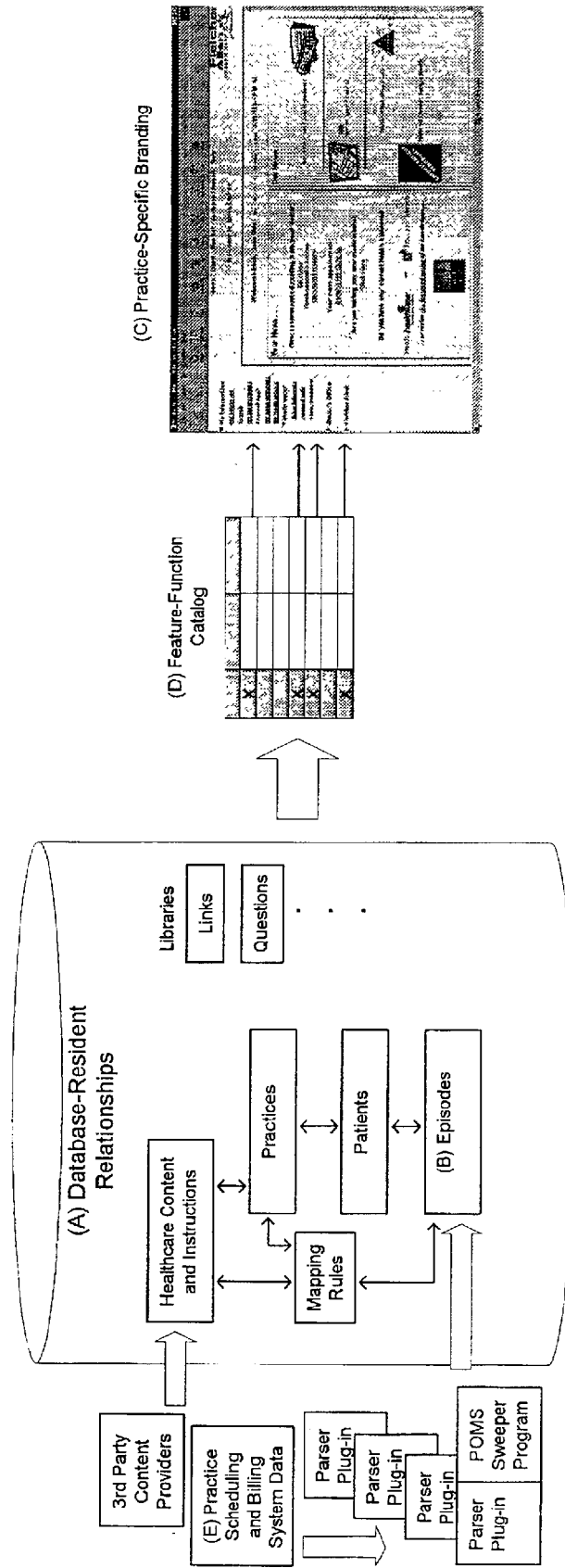
FIG. 2 is a conceptual diagram depicting the ePPi core functional architecture.

The architecture of the ePPi system incorporates the following five key methodological approaches (A–E), which when taken together, and as depicted in FIG. 2, enable the system to enhance the provider-patient communication process.

A) Database-Resident Relationships

Central to the ePPi architecture is a relational database (the DBMS, database management system) as shown in FIG. 2 that maintains information about the practices, the patients and the content in the form of related tables. Relational databases are powerful because they require few assumptions about how data is related or how it will be extracted from the database. As a result, the same database can be viewed in many different ways and spread across several tables, as opposed to a flat-file database, which is self-contained in a single table. Recording this information in a database allows the system to provide considerable flexibility, including:

- A library of standard Web site links, frequently asked questions, etc. from which the practice can choose;
- A library of rules linking standard ICD-9 and CPT-4 codes with trusted clinical content licensed from one or more third party providers; and
- The ability to extend the link-libraries on a per-practice basis, should the practice wish at a later date to provide its own content (or merely wish to change associations).

Figure 6:
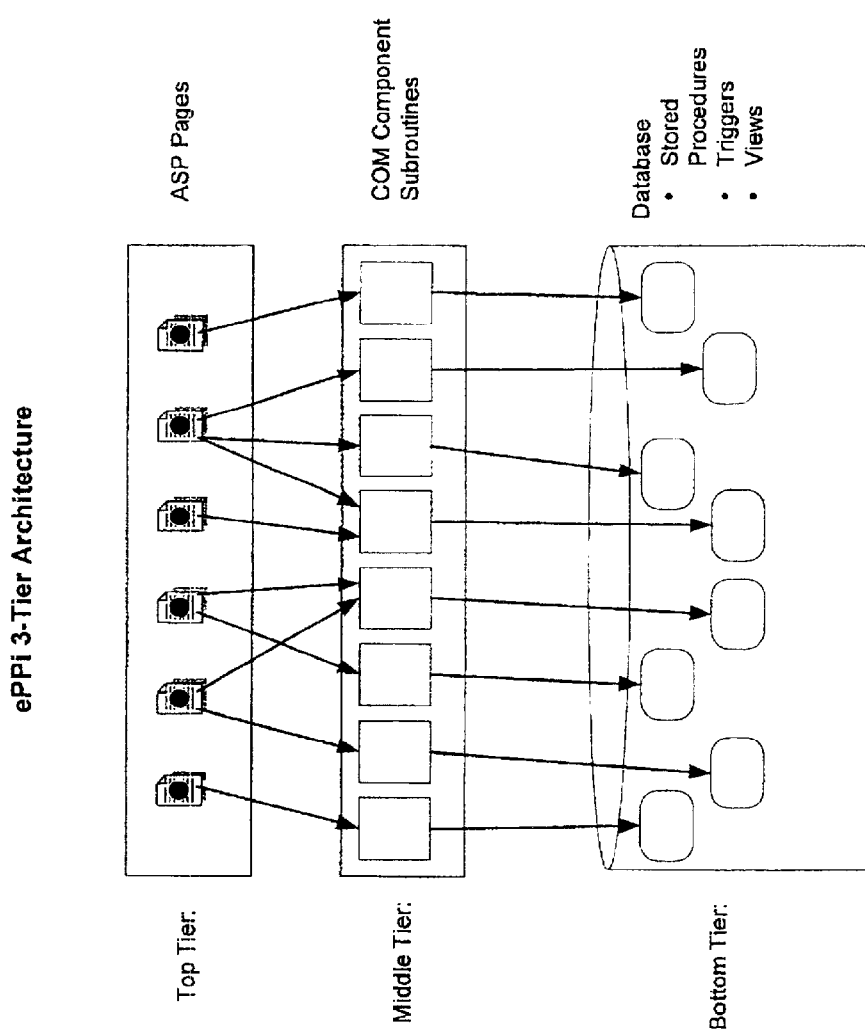
FIG. 6 is a conceptual diagram depicting the 3-tier architecture of the ePPi system, represented as follows: lowest tier=database; middle tier=component, and top tier=ASP pages.

In addition, by using a powerful relationship database engine, computation and processing of the personalized rules can be "pushed" closer to the data itself using a 3-tier architecture shown in FIG. 6, which reduces processing time, increases performance, and results in greater scalability.

B) Database-Resident Patient-Practice Episodes

"Episodes," referring to episodic events, such as upcoming appointments, as well as visits that have already occurred, are maintained in tables in the database, as shown in FIG. 2 as "(B) Episodes." Then, standard links to clinical content that are set up by the practice (or selected from the ePPi "link libraries" automatically deliver content to each patient's personal Web page (the "patient page"). A feature that makes the ePPi system unique is that delivery of the content is automatic. No additional program needs to run in the background. Merely adding the episode to the table results in the appearance of content. Moreover, the mere addition of an episode record also triggers the generation of a notification via e-mail to the patient, that something has been added to the page, further demonstrating the power and efficiency of the database engine itself.

C) Practice-Specific Web Site Branding

In the ePPi Web server, each practice site is organized according to a basic, common folder structure, with standard file names for the common content pages, graphical elements, etc. Colors, fonts and other "look and feel" elements are localized in a single definition file, and all Web pages in the site automatically inherit any change made to that file. As a result, a new Web site can be initialized, within a matter of minutes, with a standard visual theme taken from a selection of pre-defined templates. A representative page of an exemplary Web site is shown in FIG. 2 under the heading "(C) Practice-Specific Branding."

D) Feature-Function Catalog

To give each practice the ability to choose from and extend the core functionality of the ePPi system, basic user navigation elements have been designed around a basic "Feature-Function Catalog," as shown in FIG. 2. Each entry in the Catalog defines the appearance of the function in the menu, as well as the behavior when the patient user clicks on the item (i.e., a form, a static Web page, a link to an external site, etc). The default behavior of all Catalog entries is pre-defined, although a practice can customize the structure by at any time over-riding any or all of the entries, changing the order, the names, the mappings, etc. For example, as a demonstration of the power and flexibility of the Catalog structure, if a practice has already developed a personalized Web site, the ePPi system allows the practice to fully leverage that investment by creating new practice-specific Catalog entries, which "point" to those practice pages, or even over-ride the standard entries to point to those pages.

E) Practice Office Management System (POMS) Interfaces

The branding options and the feature-function catalog in the ePPi system allows each practice to customize and characterize ("brand") its own Web site. The patient-level personalization is achieved largely through the interface with the scheduling and billing systems of the practice.

The POMS interface subsystem in the ePPi system is modular, thus it is highly adaptable and can support virtually any scheduling or billing system. See, "(E) Practice Scheduling and Billing System Data" in FIG. 2. Standard data formats are defined, but if a POMS system vendor can only provide data in a particular format, the ePPi system can, as shown in FIG. 2, create a "plug-in" for the interface that merely parses the data records and hands them off to the input module. Once developed, the plug-in can be used for all practices that utilize the same POMS system.

Receipt of information about the patient into the ePPi system allows the "narrowcast" of information to that patient, based upon the way that the practice elects to map visits to the standard and custom content. By narrowcast is meant the ability of the ePPi to target content delivery and alert messages to specific patients, in contrast with the more common "broadcast" of information to large groups of users. The ePPi system leverages the patient episodic data, and the database-resident relationships, to deliver content to individual patients, based on practice-specific rules and practice-specific site branding and formatting options. The POMS interface delivers the episodic data to the ePPi Service Center, thus providing the raw material upon which the ePPi acts (see, FIG. 2).

FIG. 2 further illustrates how methods A through E interact at the core of the ePPi to provide a unique and customized interactive experience for every patient and every provider. As shown in FIG. 2, the POMS practice scheduling and billing data (E) enter the parser plug-in(s), are parsed, filtered and stored in (B) the repository of patient-practice episodes. Subsequently, the rules of (A) the database-resident relationships are used to present HTML Web pages to patients according to the options defined in (D) the feature-function catalog, with a practice-specific customized look-and-feel defined according to (C) the branding options.

It is also envisioned that some or all of the elements of a Web page of the present invention can be conveyed to the user aurally (by a speaker set, for example) or by tactile or olfactory means as well as on a display screen. This would be particularly useful for handicapped patients, such as blind patients. The system can also be readily adapted to transmit information in foreign languages, as necessary.

The value of the ePPi system has broad applications. For example, data from the test sites has proven that patients respond and alter their behavior when they receive instructions from their own physician. In fact, when a flu shot reminder was sent out in a test case, over 60% of the on-line patients in the service visited the site within 24 hours. More importantly, 30% of the patients attending a subsequent focus group reported that they got the flu shot as a result of the notice. This type of influence is also of significant value to companies, such as pharmaceutical manufacturers, who stand to generate significant additional revenue from improved compliance from their existing customers.

Accordingly, if advertisers are granted direct access to the patient (the doctor will always control the decision as to whether a third party will be granted access to their site) the vendors can make the patient aware of and provide the patient with the opportunity to purchase their products on-line. Thus, the site offers a unique opportunity, in selected circumstances, to provide access to advertisement and/or e-commerce.

Much like physicians, case managers and payment systems (such as Blue Cross) are also looking for ways to provide information to, and enhance compliance from, member patients for whom they carry the financial risk. Use of the ePPi system in such instances would apply the same principles as described above, except that the data would be drawn from the payer's claims database, and patient interaction would be with the case manager.

Call centers offer services wherein patients can talk to a trained professional, such as a nurse or midwife, about a particular health problem. The discussion may result in referral of the patient to a physician or additional measures may not be necessary. A great deal of time in a typical medical practice is spent in triage during the question and answer period, and even more collecting pre-visit information in the case of a referral. However, by using the ePPi call center module, the time required for triage by the nurse may be reduced by as much as 50% by automating much of the question and answer and pre-visit data collecting process. This service translates into significant capacity gains for the call center, and in more privacy and flexibility for the customer or patient.

Patients are in many circumstances asked to, and in fact, prefer to monitor their own health care at home using a variety of home monitoring devices. Such devices often have the capability to plug directly into a local PC and automatically download data. The ePPi system provides modules and home-monitoring device interfaces to pick up data from the patient's PC and transfer it to the physician, practice, or service. The system further provides the capability of establishing an interactive process with the doctor, practice or service to facilitate warnings, feedback and the like between the patient and the doctor.

In addition, although there is not currently a link between prescription ordering and prescription filling or delivery, ePPi allows physicians to order new prescriptions or for patients to order authorized prescription refills directly from a member pharmacy through the system interface. By using automatic prescription pads in the office, physicians can interact directly with the pharmacy, thereby facilitating direct delivery of the medication to the patient, but more importantly eliminating many of the errors (some of which are life threatening) that currently occur when hand-written prescriptions are filled. As a confirmation, the patient is provided with a written summary of each of the drugs or medications being taken, thereby permitting the doctor to warn of dangerous drug interactions and the pharmacy to provide the necessary instructions or warnings, as refills occur. This service is particularly valuable to the elderly or handicapped patient, or to the parent of a sick child.

These and numerous additional functions, although they may not be currently activated in the present versions of the ePPi system, nonetheless exist and can become operational with minor programming updates of the present system. It is intended that these functions also are encompassed by the present invention, so long as the basic ePPi system remains functional as herein described.

Clearly, the ePPi system refers not only to a product, but also to a service, both of which are delivered at/from the following 3 main elements.

1) The Service Center

Figure 3:
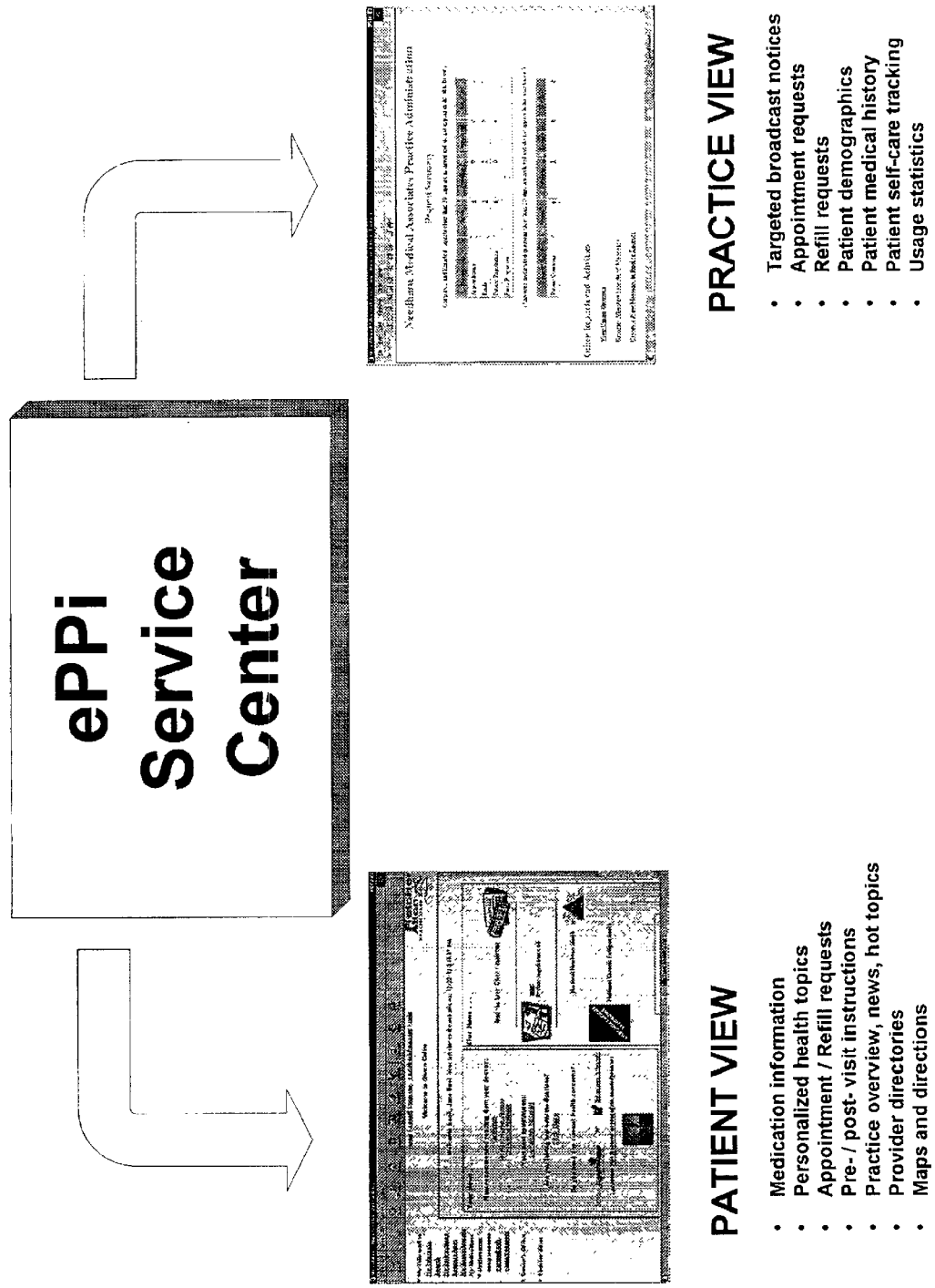
FIG. 3 is a conceptual diagram depicting the Practice View and Patient View functional output of the ePPi Service Center, which comprises a Web server; a database server; a modular data collection and storage program; and an electronic mailing capability to support automated transmissions.

The "Service Center" includes, but need not be limited to, management and administration by the ePPi system administrator of the Web Site design and hosting, the standard content subscriptions, the practice-supplied content, the continuous content updates, data security and encryption, project planning, implementation management and patient roll-out strategies. As detailed in FIG. 3, service is the heart of the ePPi solution. Pre-established components, such as the feature-function catalog and patient instructions, combined with the ePPi implementation team allow the practice to deliver a comprehensive information service to its patients without requiring them to develop or acquire marketing or technical expertise. The service begins with the set-up process at the practice, and continues with the delivery of data to its patients, as shown in FIG. 3.

The ePPi system comprises a set of one or more server computers, which perform various tasks. These computers may or may not necessarily be co-located in a single facility, although they are collectively referred to as residing in the "Service Center" (see, FIG. 3). Regardless of their physical location, they comprise a logical unit, working in concert to provide the ePPi functionality. As shown in FIG. 3, the functional components of the ePPi Service Center include: a Web server capable of responding to HTTP requests from users; a database server capable of maintaining complex relationships among practices, patients, doctors, and healthcare informational content; a modular data collection program that receives, reformulates and stores information from doctors'or practitioner's scheduling and billing systems regarding patient visits; an electronic mailing capability which supports the automated transmission of notifications to patients and transmissions to the practice.

Furthermore, the architecture has been designed with maximum flexibility in mind, so that the ePPi Service Center may be scaled appropriately to the needs of the users. Thus, it may be required to have more Web servers and fewer database servers, or more database servers and fewer Web servers. A single computer can host a single functional component, or it may host a combination.

Initially, one operator workstation administers the system. As the need arises for additional workstations to provide increased capacity, additional operator workstations can be added by adding additional computer systems, installing the administration software, and connecting them by, e.g., LAN.

2) The Patient View

The "Patient View" includes, but need not be limited to, management of medication information, personalized health topics, appointment/refill requests, pre- and post-visit instructions, practice overviews, news and "hot" topics, provider directories and maps and directions. As detailed in TABLE 1, the Patient View component: allows patients to retrieve information at any time, from any location, so long as there is Internet access. However, the features provided in TABLE 1 are intended only to be exemplary, and the invention need not be in any way limited. The Patient View is tightly secured as an encrypted communication for patient specific data. The View is extremely simple to use, and it presents information that is tailored to the patient's specified interests and based upon the patient's relationship with the participating physician.

TABLE 1

Detailed features and benefits from the Patient View.

| Feature | Benefit |
| --- | --- |
| Broadcast Notifications | |
| Receive healthcare reminders via e-mail from the doctor's office | Patients have increased awareness of healthcare issues of personal significance. |
| Notices are filtered and personalized based on the patient's age, gender, and/or interests. | Improved adherence to advice/instructions provided by the doctor. |
| Areas of Interest & Prescriptions | Simple to view - all data is pre-formatted and arranged based on the patient's preferences. |
| Pre-packaged, easy to understand data including: Self-care instructions Pre-filtered health care topics Prescription information | No "surfing" - topics important to the patient are displayed with single mouse click. No nonsense access to quality information, pre-approved by the practice. |
| Pre & Post-Visit Information | Clinical content related to specific visits is available any time. |
| View a list of: Upcoming or previous visits with specific instructions The scheduled provider for the visit The location of the visit How to prepare for a first visit or test What to bring | Information is available without having to use the phone or wait until the practice is open. Fewer forms to complete and less time spent in the waiting room. Patients can prepare for the visit before they arrive. Fewer rescheduled tests because of unprepared patients. |
| Forms/Data Collection | Request appointments, refills or callbacks at any time. |
| Customized forms allow patients to input any sort of data: Appointment, refill or call back requests Demographics Medical history Daily health monitoring | Questions are answered without having to wait for the doctor's office to call back. Reduced time in the waiting room because forms are filled out in advance, according to the patient's schedule in the privacy of his/her or her own home. Eliminate unnecessary screening visits with medical support staff. |
| General Information | Greater access to facts about the practice and the providers. |
| The patient can view: Practice overviews Provider directories Interactive maps and directions Frequently asked questions Hot topics Practice news | Patients learn about the practice on their own schedule. Directions are easily accessed and printed for use at the time of travel. Patients are made aware of topics or events that they might not have without this type of access. Questions are answered without having to call the practice. |

3) The Practice View

The "Practice View" includes, but need not be limited to, management of targeted broadcast notices, handling of appointment requests, handling of prescription refill requests, patient demographics, patient medical histories, patient self-care tracking and usage statistics. As detailed in TABLE 2, the Practice View allows the doctor and/or his/her staff to receive information from and send responses and related information back to the patient. However, the features provided in TABLE 2 are intended only to be exemplary, and the invention need not be in any way limited. Standard functions include targeted broadcast notices, requests for appointments, prescriptions and call-backs, or completed patient demographic, medical history or compliance forms. By using the ePPi system, the practice benefits from fewer interruptions and more complete and accurate patient information. The ePPi system employs secure certificates technology to ensure that administrative functions within the Practice View can only be accessed by authorized staff from secure workstations.

TABLE 2

Detailed features and benefits from the Practice View.

| Feature | Benefit |
| --- | --- |
| Broadcast Notifications | |
| The practice can generate, filter and send health notices to subsets or all of their patient population. Notices are filtered and personalized based on the patient's age, gender, and/or interests. | Patients have increased awareness of healthcare issues of personal significance. Patients are more adherent to advice/instructions provided by the doctor. |

TABLE 2-continued

Detailed features and benefits from the Practice View.

| Feature | Benefit |
| --- | --- |
| Appointments & Callbacks | |
| Presents the practice with patient requests for appointments, prescription refills, callbacks, etc. On-line requests allow the practice to manage workflows more efficiently. Requests can be:<br>Routed directly to the designated practice<br>Sorted by urgency, availability etc.<br>Printed for Medical record filing<br>Health Maintenance Forms | Reactive work is turned into managed workload E-mail replies can be sent without having to "reach" the patient.<br>Reduced time on patient follow up.<br>Significant reduction in incoming and outgoing telephone traffic. |
| Data from electronic forms received from patients can be used to avoid screening visits and track patients' progress. Data can be:<br>Viewed<br>Sorted<br>Printed<br>Filed<br>Usage Statistics | Patient information is packaged and delivered more completely and accurately as a result of automated editing.<br>Improved patient compliance with self-care practices.<br>Fewer unnecessary visits |
| Reports are provided to the practice on patient usage including most popular functions | Statistics received can be used to optimize services offered through the Internet. |

Further, the system offers information in essentially real-time since the system can be routinely updated at the end of each day of patient visits.

III. Design Specification for the ePPi System

The ePPi system presents its Patient View and Practice View by means of a database-backed Internet application running on a Web server. In the preferred embodiment, the database management system is Microsoft SQL Server, and the Web server is Internet Information Server (IIS) with additional enhanced features provided by Site Server; all of these programs are the product of Microsoft Corp. and they feature a high degree of interoperability. The preferred development tools and languages include Microsoft's Active Server Pages (ASP), with programming logic scripted in VBscript and JavaScript.

The reminder of this section III provides detailed descriptions of how the inventors have used the preferred platform (database server, Web server, and development tools) to realize the functionality of the ePPi system. In light of these descriptions, developers who are knowledgeable in the art can, without undue effort, also implement the ePPi Patient View and Practice View using known alternative database and Web server technologies, in combination with known alternative development tools and programming languages.

A. Shared Pages and Components

Microsoft's ASP technology permits the developer to embed extensive logic within each document on the Web server. The IIS Web server reads and interprets the scripted logic, strips out the script statements, and delivers an HTML formatted document to the requesting Web browser. The ASP technology includes the ability to dynamically alter the final content of the document that is delivered, based on information stored in a database, as well as information collected from the user during the current Web session.

In the preferred embodiment of the invention, much of the core functionality of the Patient View and the Practice View is implemented within ASP pages corresponding to each function. The logic that is scripted in each page, as well as the data and relationships that reside within the database, permit the ePPi to dynamically assemble and deliver custom content into these ASP pages, uniquely for the user who is requesting the document.

For example, a page that displays a list of upcoming appointments for the current user need only be developed once, with scripted logic to retrieve the user-specific list of appointments from the database. The list is then presented as part of the formatted HTML document that is sent to the patient user's Web browser.

Furthermore, the overall "look and feel" of the page—the colors, fonts, and graphical elements that constitute the "branding" of the site based on the specific practice's preferences—can be applied dynamically to the page when it is delivered to the user's Web browser. The branding of the site makes it unique and identifiable to the practice.

By recognizing the differences among (1) core functionality within the Patient View or Practice View; (2) patient-specific information that can be dynamically retrieved from the database; and (3) practice-specific branding that can be applied when the page is delivered, many of the Web pages that deliver core features and functionality within the Patient View and Practice View are implemented only once, yet they look different depending on the practice, and on the user.

These "shared" pages reside, in the preferred embodiment of the invention, within a specific directory on the Web server that is accessible no matter which practice's web site is being presented. Additional shared components that may be needed by developers knowledgeable in the art—for example, server-side "include" files, and COM components, likewise reside in this Shared directory or in logical subdirectories.

B. Web Site Domain

Each "registered practice" or "customer" (clinic, large practice, collection of small practices, etc.) in the ePPi system has a logically distinct web site. Multiple web sites might co-exist on the same server, or a single site might reside on its own server.

As used in the preferred embodiment of the invention, the term "Customer Domain" refers to the logical collection of web pages that presents a particular registered practice's content, and also to the corresponding physical subdirectories and files that constitute the HTML and Active Server Pages(ASP), and any component objects used therein.

Although much of the core functionality of the ePPi Patient View and Practice View can be implemented in shared ASP pages using scripted logic, there is certain content for each practice that is totally unique to that practice, and that is static (i.e., does not change depending on the user who is requesting the document). For example, a page might contain photographs of a doctor's office, address/phone information, driving directions and a map. Such a page is best implemented as a static HTML document within the Customer Domain, rather than as a dynamic ASP document in the Shared area.

In the preferred embodiment of the invention, the Customer Domain is organized into subdirectories as follows:

/Content

The Content subdirectory contains individual HTML document page files that contain content about the practice. Certain "standard" files may exist for a practice, using default names, as defined in the Feature-Function Catalog (detailed below). However, any page may reside in the Content subdirectory, having any name; these pages could be accessible via hyperlinks on other pages, or via hyperlinks on the navigation menu as defined in the Feature-Function Catalog for the practice.

The Content subdirectory may contain additional subdirectories of its own, in order to logically group pages of a particular content type. Such grouping is entirely discretionary. For example, a separate HTML page could be formatted to describe each doctor within a practice (containing a biography, photograph, etc.). For a practice with a large number of physicians, these staff pages could be stored within a Staff subdirectory below the Content subdirectory.

/Content/Images

At a minimum, each Customer Domain uses a /Content/Images subdirectory where image files reside that are embedded in the practice's static content pages. Interactive forms that involve customization on a per-practice basis are grouped together in a special directory within the Customer Domain.

/Forms

Some form pages are used for standard features within the ePPi Patient View, such as requesting an appointment. Others are used to provide functionality unique to the practice, such as a form for gathering particular details about a patient's medical history.

C. Overall Practice Site's Look and Feel

The ePPi user interface design objectives are targeted at users who are patients, who are somewhat familiar with using a computer and an Internet browser, but who otherwise do not have extensive computer usage experience. In the Patient View, all pages within a particular Customer Domain exhibit a consistent "look and feel," which may or may not be commercially recognized or "branded."

Figure 4:
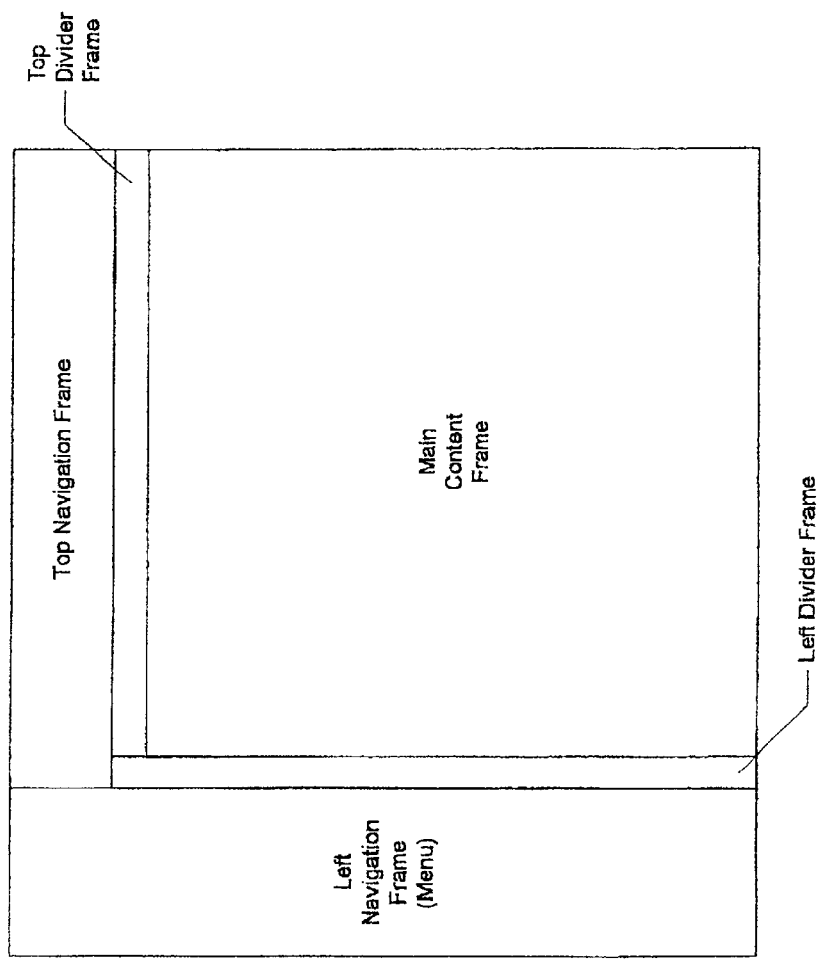
FIG. 4 depicts the basic Patient View screen layout using 5 HTML "frames."

In the preferred embodiment of the invention, HTML frames are'used to partition each page into standard and dynamic regions (see, e.g., FIG. 4). The use of frames results in faster overall response to document requests from the user's Internet browser, because portions of the screen that are static (such as the menu of navigation links, the practice logo, etc.) do not need to be re-sent from the Web server; only the new content information frame needs to be generated.

The basic screen layout, using 5 HTML "frames" is set forth in FIG. 4. The top portion of the screen contains a frame with a set of standard navigation hyperlinks such as "Home Page," "Login," "Help," etc. The practice logo and name may also appear in the top frame, based on the practice branding options.

The left portion of the screen contains a frame with a scrollable list of hyperlinks, each corresponding to a feature of the ePPi Patient View. The exact contents of the navigation menu depend on how the Feature-Function Catalog has been configured for the practice. The left frame can also contain a practice logo, or other text and graphics, based on the practice branding options.

Just below the top frame, a horizontal "divider" frame can be defined to provide spacing or a border between the top navigation area and the main content area. Likewise, a vertical "divider" frame next to the left navigation frame can also be defined.

The remaining portion of the screen (representing the bulk of the page "real estate") contains the content for the currently selected feature from the navigation menu (or subsequent page if the user clicked a hyperlink inside another content page). Thus, at any given time, the main content frame may be displaying a static HTML page (from the Customer Domain subdirectories), a dynamic ASP page (from the Shared subdirectories), or possibly even an external page, not even hosted at nor served by the ePPi Web server.

When a user is viewing pages from the Customer Domain, or shared dynamic ASP pages, they must be presented with a consistent "look and feel" that must coordinate with the way that the top and left frame are displayed. Text font and colors, background colors, graphical elements, and the like, are all coordinated. Collectively, these elements and stylistic decisions constitute the site "branding" options for the practice.

Graphical elements that appear in the top and left frames or on shared ASP pages can be made different for each practice by observing consistent naming conventions. For example, a file called "LOGO.GIF" located in the same subdirectory of each practice's Customer Domain can be referenced from any shared page. Each copy of the file is different because it contains the graphical logo for the corresponding practice, but the name is always the same. Consequently, the proper practice's logo appears on the shared page, regardless of which practice Web site is visited.

All such practice-specific graphical elements are grouped under a specifically named subdirectory within the Customer Domain:

/Theme/Elements

In addition to the practice logo, other examples of such graphical elements include form buttons (such as "Login," "Sign Up," "Preview", navigation buttons ("Go to Top of Page", indicators ("New," "Recommended by Your Doctor" and any other graphical elements that may be defined for use on shared pages. By making them configurable for each practice, they can be color- and theme-coordinated with the overall look and feel of the site for each particular practice.

In addition to the graphical elements that may be different from one practice to another, the selections of colors, page backgrounds, fonts, etc. are also configurable per practice. In the preferred embodiment of the ePPi, the inventors have elected to utilize linked style sheets in all static pages (residing within the Customer Domain) as well as all dynamic ASP pages (residing within the Shared directory). The linked style sheet has the name STYLE.CSS and is present in the following subdirectory within each Customer Domain:

/Theme/Style

By "style sheet" is meant a file or form that defines the layout of a document, in which parameters, such as the page size, margins and fonts are specified. Style sheets are useful because the same style sheet can be applied to many documents. Practices can even elect to alter their overall look and feel at different times of the year (e.g., the holiday season) in order to keep their patients'interactive experience fresh and interesting. Style sheets may be "embedded" or "linked." A "linked" style sheet is a separate, self-contained file containing all of the style definitions. Practices electing to use different styles on their Web pages merely reference the style sheet file name (link to it). Thus, with essentially no effort, a change in the style sheet is immediately and automatically reflected in all pages that link to the style sheet.

Using a style sheet makes it possible to configure virtually all visual aspects of the fonts, colors, and backgrounds, as well as hyperlink colors and "rollover" behavior, independently in each of the frames that make up the page layout. However, developers reasonably skilled in the art can also use known alternative approaches for dynamically establishing branding of the site for each practice.

D. Feature-Function Catalog

The ePPi Patient View includes many features for provider-patient interaction; however, not every practice will necessarily want to offer all features to its patients. Furthermore, practices may wish to change the labeling of their selected features in the navigation menu, and also offer additional unique features in the menu, such as links to statically maintained pages. To provide the required level of flexibility in the configuration for each practice, the ePPi uses a Feature-Function Catalog, whereby the behavior of each practice's menu is configured.

An effective analogy for the Feature-Function Catalog is a library "Dewey Decimal System" for classifying books. Categories and sub-categories of book subjects are defined using a standard numerical system. A specific library (a Customer Domain) will choose to stock certain books, and may choose to include or exclude specific categories or sub-categories. A patron of the library (or a patient who accesses an ePPi web site) can access books in any of the categories offered by the library, but does not see the categories which the library chooses not to offer.

The Catalog is defined with various default values, corresponding to commonly used features within the ePPi Patient View, in order to make the configuration easy when a practice site is set up. However, any attribute of any feature within the Catalog may be overridden, and entirely new custom features may be defined for a specific practice and intermixed with the "standard" features within the menu.

For each Feature, the Catalog defines, at a minimum, the following attributes:

the unique "Catalog ID" for the feature;

the text or graphical label that appears in the menu;

the text that appears at the top of the page when the menu item is clicked and the page is displayed;

the location (Shared, Customer Domain Content, Customer Domain Form, External);

the actual file name of the HTML document or ASP dynamic page that is delivered to the Web browser when the user clicks the menu label; and whether to display the page using standard HTTP or HTTPS (secure socket layer—SSL).

By convention, all features in the Patient View that involve the display of patient-specific information are configured in the Catalog as SECURE pages. Because SSL involves extra overhead, it is best to use it only when needed; thus, the static HTML pages in the Customer Domain are configured by default for non-secure display. However, the security attribute, like all others, is independently configured for each feature in the Catalog.

Catalog ID's are 6-digit values and are grouped into "families" with default menu labels, according to the first 3 digits, as follows:

001xxx are features relating to the PRACTICE information, such as staff listing, and office locations 002xxx are features relating to the specific PATIENT who is logged in, such as upcoming appointments and requesting prescription renewals 900xxx to 999xxx are set aside and may be used to define any arbitrary group for a particular practice As features and functionality are added to the ePPi Patient View, additional Catalog ID's are defined within the 001 (practice) family and the 002 (patient) family, and additional families are also defined.

Within each feature family, the last 3 digits of the Catalog ID define the actual feature, and entries 001900 to 001999 and 002900 to 002999 are set aside and may be used to define any arbitrary individual feature for a particular practice.

Features that are pre-defined with default values in the Catalog may be used without the need to override any of the attributes. If desired, individual attributes of any Feature may be overridden without the need to explicitly define ALL of the attributes of that feature. Furthermore, entirely new features can be defined for any practice, by using Catalog ID numbers that have been "reserved" for this purpose.

Once the desired Features have been determined, and any default overrides have been specified, the menu for a practice Web site can be completely specified simply by editing the practice configuration file to specify the feature family (ies) that are desired, and the specific feature(s) within each family.

As an example, Table 3 shows a subset of the default Feature-Function Catalog.

TABLE 3

A Subset of the Default Feature-Function Catalog.

| Catalog ID | Menu Label | Page Title | Location | Page File | Security |
|---|---|---|---|---|---|
| 001xxx | Practice Info | n/a | n/a | n/a | n/a |
| 001004 | Staff | Doctors and Nurses | CONTENT | docnur.htm | no |
| 001005 | Q and A | Frequently Asked Questions | SHARED | pcontent.asp?type=5 | no |
| 002xxx | My Information | n/a | n/a | n/a | n/a |
| 002006 | Request Appt | Request Appointment | FORMS | requestappt.asp | yes |
| 002008 | My Interests | Areas of Interest | SHARED | articles.asp | yes |
| 002011 | Ask a Question | Ask a Question | SHARED | myquestions.asp | yes |

A particular practice could be configured to offer all of these features in its menu, using all of the default values, simply by specifying, for example, the following settings in the practice configuration file:

TOPICFAMILIES=002,001

TOPICS002=008,006,011

TOPICS001=004,005

With only those 3 lines in the practice configuration file, the practice Web site menu appears as follows (note the hierarchical nested grouping of features into their families):

My Information
  My Interests
  Request Appt
  Ask a Question
Practice Info
  Staff
  Q and A On the other hand, the practice configuration file may be edited to contain, for example, the following settings:

TOPICFAMILIES=002,001
  TOPICS002=008,006,011
  TOPICS001=004,005,901
  Label200=About Me
  Label001=About My Doctor
  Label002006=I Need an Appt
  Label002011=I Have a Question
  Label001901=Employment
  LocationCode001901=EXTERNAL
  Page001901=www.someotherplace.com/employment.html The effect is that a new practice-specific feature is added using a reserved Catalog ID, and some of the "default" settings of the standard Catalog entries are overridden. Consequently, the practice Web site menu then appears as follows:

About Me
  My Interests
  I Need an Appt
  I Have a Question
About My Doctor
  Staff
  Q and A
  Employment E. Security Features p Much of the content presented through the Web interface relates directly to the patient's medical situation, and as personal information, must be handled as secure data. Specifically, a patient's past visits, upcoming appointments, prescription list, form-fill data, and selection of areas of interested are considered confidential. By default, all Features within the PATIENT family of the Catalog (002xxx) are accessed using a secure, encrypted connection, although the secure connection is not necessary for accessing other areas of the site, since the other areas are more generic in nature. As the patient navigates into, or out of, the features in the 002 family, the server initiates or terminates secure connections. The patient's Web browser may provide feedback to the patient when this happens, depending on the run-time options of the browser. However, the overall experience to the patient is much the same as ordering or purchasing an Internet-based product or service using a credit card using known procedures.

The nature of the Internet makes it possible for any individual to access any Web site, provided they know the URL of the Web site. The ePPi Web server displays any non-secure page (as defined in the Catalog for the practice) to any user who accesses the practice site. It is not necessary for a user to "login" to the Web site in order to view information, such as practice office hours and locations.

For patient-specific content, the ePPi Web server must know the identity of the patient in order to customize the content presented. A login page is presented, where the patient enters his/her name and password. The login page includes a "remember my password" checkbox, which stores the password on the patient's computer in a "cookie" file. Persistent Client State Cookies ("cookie") refers to a file stored on the patient's computer, which contains state information, such as user names, preferences, or a unique member identification code.

As described above, however, an exception to the strict security rules applies to families, wherein the application security is expanded to address family relationships. As a result, a parent can view the appointment and prescription information for his/her child.

In order to validate a patient's login attempt, the user's name and password must exist in the ePPi database. Patients may fill in a sign-up form that is accessible via a hyperlink from the top frame. The form requires that the patient supply various demographic information, to including, but not limited to, his/her e-mail address, social security number, and medical record or other unique identifying number.

Once the user has entered the required information, the ePPi checks for the existence of the patient in a "repository" population table. The repository is populated through the periodic receipt of data files from the practice's office management systems (POMS), described in a subsequent section below.

If the user's two unique identifiers (e.g., social security number and one other) both match a record in the repository, the ePPi automatically assigns the user a unique user name and password, and sends a "welcome on-line" e-mail message to the user with instructions for first-time login. The ePPi also activates any upcoming or prior appointment information in the repository, so that even upon their first login, the patient sees customized content based on his/her visits to his/her own doctor's practice.

If an exact match cannot be found for the user who has signed up, the information collected from the sign up form is held in an exception list. Then, an administrator at the practice has the ability to manually review the list and either validate or reject the sign up request, via the ePPi Practice View.

F. Database Architecture and Schema for Dynamic Data

Figure 5:
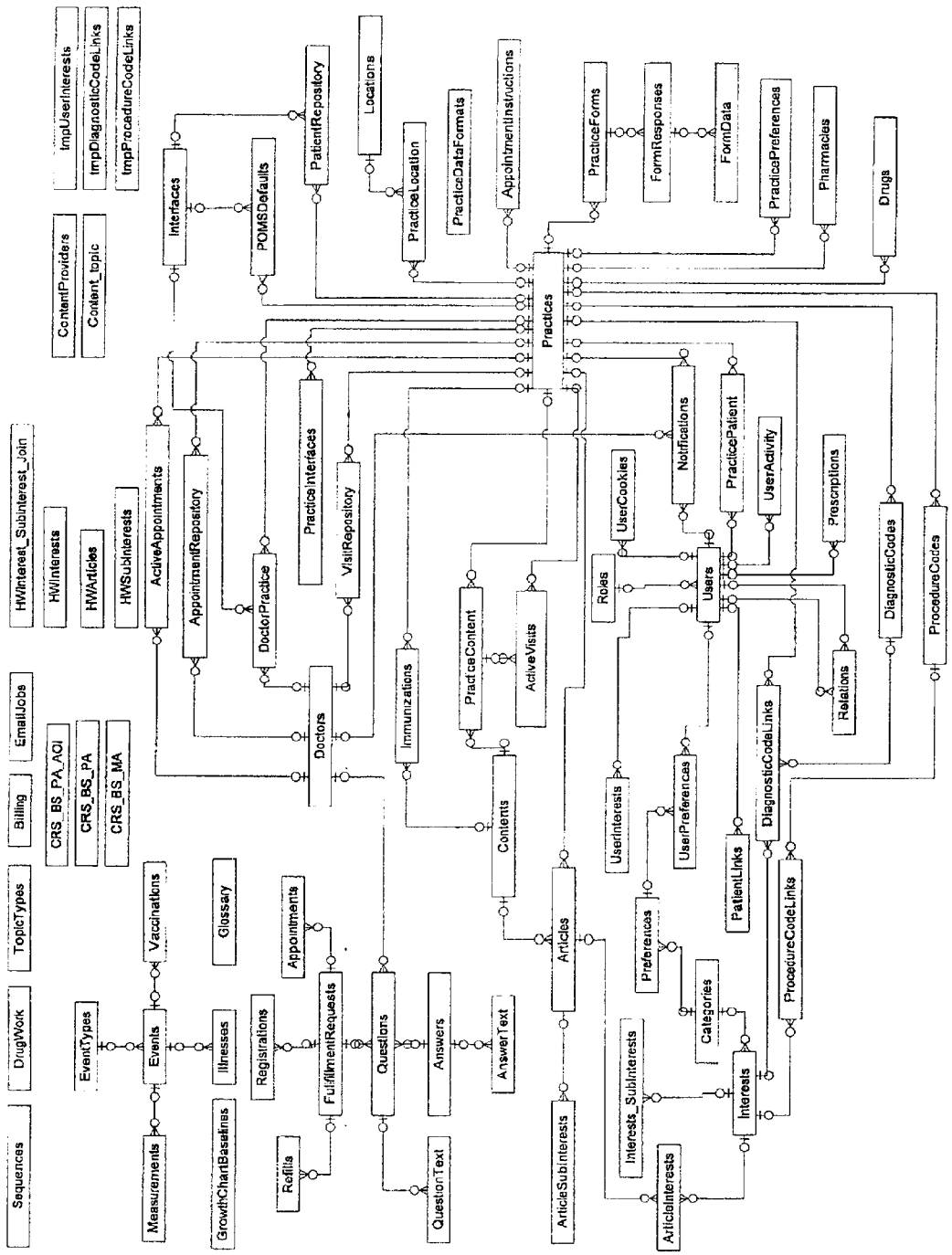
FIG. 5 depicts the schema tables resident in the ePPi database, and the explicit relationships between the tables.

The schema diagram shown in FIG. 5 depicts tables resident in the ePPi database, and the explicit relationships between the tables. The tables can be grouped into the following conceptual categories corresponding to various core elements of the ePPi functionality. Some tables serve multiple functional purposes, and are therefore included in multiple categories.

1. Practice Subsystem

The Practice Subsystem of the ePPi database maintains information about each practice, including practice-specific preferences. The tables involved in this subsystem include:

Practices, PracticePreferences (basic information about the practice, such as its name; the preferences can affect a variety of run-time behavior and are stored in a table for extensibility without the need to alter the database schema);

Locations, PracticeLocation (information about each different geographic practice office location);

PracticeDataFormats (practice-specific data format information);

PracticePatient (mapping of users in the User Subsystem who are patients of the practice or, in the case of pediatric and other guardian/relation practices, responsible parties of patients of the practice);

Pharmacies (listing of pharmacies in the area served by the practice);

Doctors, DoctorPractice (listing of doctors associated with a practice, and their codes in the practice's scheduling and billing system(s));

Drugs (links to content items relating to drugs that the practice specifically wants to let patients learn about);

Immunizations (practice-specific immunization schedule with links to content items about each vaccine);

PracticeContent, TopicTypes (links to content items for practice-specific frequently asked questions, news items, recommended links, and health topic search mechanism);

AppointmentInstructions, DiagnosticCodes, ProcedureCodes (links to practice-specific content items relating to pre-visit appointment type codes and post-visit billing codes);

DiagnosticCodeLinks, ProcedureCodeLinks (links to interests that can be directed to patients as recommended reading based on their post-visit billing codes);

PracticeForms, FormResponses, FormData (information collected from users via on-line form in the practice Web site); and PatientRepository, AppointmentRepository, VisitRepository (list of users who are permitted to sign up to use the practice Web site, and their known upcoming and prior visits).

2. Content Subsystem

The Content Subsystem is the central store of all practice-specific and generic content that is displayed to the user based on practice-specific links and patient-specific episodes.

Contents (the main index of content; each entry can include the content itself if it is small, or a pointer to the content if it is large or hosted on an external Web site);

Articles, ArticleInterests, ArticleSubInterests, Interests, Interests_SubInterests, Categories (index of healthcare articles that users can read, catalogued to permit selection based on user interests that are specified explicitly by the user or automatically to drive recommended reading based on user visits); and Glossary (glossary of healthcare terms that can be searched by users).

3. User Subsystem

The User Subsystem stores information about each user, including their preferences, interests, and episodes relating to the practice.

Users, Roles, Relations (user names, password, demographic details, role-based access rights to features within the ePPi system, and parent/child or other guardian-type relationships);

Preferences, UserPreferences (the preferences can affect a variety of run-time behavior and are stored in a table for extensibility without the need to alter the database schema);

UserInterests (mapping of interests selected by the user manually or automatically added as recommended reading);

ActiveVisits, ActiveAppointments, PatientLinks (episode information: upcoming appointments and prior visits received from the practice scheduling and billing systems);

Notifications (record of all notifications sent out to patients, including initial welcome message, appointment reminders, and all alerts that there is new personal information on the practice Web site for them); and UserCookies, UserActivity (links used to relate user demographic and activity information with Site Server logs).

4. User Event Subsystem

The User Event Subsystem records event-related data that may be entered by the user or received through an interface from the practice or other source.

Events, EventTypes (basic list of all user-specific events);

Prescriptions (current or archived medication that the user is taking or has taken, with start and end dates);

Illnesses (list of illnesses with onset and end dates);

Vaccinations (dates when the user received various vaccinations);

Measurements (measurements such as height, weight, and head circumference, with the date of recording); and GrowthChartBaselines (percentile baselines used to produce graphs of individual patient measurements).

5. User Request Subsystem

The User Request Subsystem tracks the details and status of all fulfillment requests entered by the users, which the practice responds to via the ePPi Practice View.

FulfillmentRequests (central tracking table of all requests);

Refills (details of prescription renewal requests);

Appointments (details of new appointment requests);

Questions, QuestionText, Answers, AnswerText (details of questions entered by patients); and Registrations (details of sign-up requests).

6. POMS Interface Subsystem

The following tables support the loading of episode data received by the POMSSweeper program from practice scheduling and billing systems.

Interfaces, PracticeInterfaces, POMSDefaults.

7. Content Update Support

The following tables support the automatic processing of scheduled periodic updates from third party licensors of healthcare content contained within the ePPi database. This section of the database is extensible to support licensing arrangements with additional content providers.

ContentProviders, Content_topic;

HWxxxx, tmpxxxx, DrugWork (tables used to process updates from Healthwise); and

CRSxxx (tables used to process updates from Clinical Reference Systems).

8. Miscellaneous Support

The remaining tables provide miscellaneous support functions, such as analysis for customer billing and control of e-mail notification processes.

G. Database Gateway Component

In the preferred embodiment of the invention, ASP technology is used to dynamically assemble HTML documents based on content retrieved from the database regarding the current user and practice. Although it is possible to interface directly to the database from the ASP page, using actual structured query language (SQL) statements embedded in the scripted code, the inventors have implement a 3-tier architecture for its added robustness, scalability, and security. As shown in FIG. 6, the 3-tier architecture is represented as follows: lowest tier database; middle tier=component, and top tier=ASP pages. In FIG. 6, the Database Gateway Component acts as a pass-through interface between the ASP pages (top tier) and database management system (bottom tier). In the preferred implementation, virtually all of the program logic for database updates and retrievals resides in the database itself, using stored procedures. However, developers reasonably skilled in the art can implement the logic at any one of the 3-tiers.

H. Notifications

Among the patient-selectable preferences is the option to receive an e-mail notification whenever a new content item is added to the database. If the preference is enabled, e-mail notifications are sent to a patient based upon, for example, the following content types:

New articles that match the patient's stated areas of interest;

New practice-supplied content (news, frequently asked questions, hot topics); and New appointment or visit information received from the practice management system interfaces.

As additional features and functionality are added to the ePPi Patient View, and as the ePPi Service Center expands to accept content from additional third party content providers, the types of content updates that drive patient notifications can likewise expand.

The e-mail notification indicates that new content is available on the Web site, and includes a convenient hyperlink within the body of the message. Clicking the hyperlink invokes the patient's Internet browser, and goes directly to the practice Web site, where the patient can login in order to view his/her customized content over a secure Internet connection.

When the patient submits a form (to request an appointment or callback, pre-visit form, health tracking, etc.), the ePPi sends an e-mail message to the practice indicating that a patient request has been made. Practices can also designate the e-mail address to be used, which will generally not be that of the patient's doctor. For example, when patients call their doctor's office to ask a medical question, the question is typically fielded by a triage nurse, who consults with a doctor as needed. The ePPi permits analogous coverage designation for e-mail notifications.

I. ePPi Service Center Operations

The ePPi system Service Center exists conceptually as an "assembly line" of steps that receive and prepare content for inclusion in the ePPi system database. Once the information is in the database, the patient/practice relationships dictate which patients are permitted to see which information. Physically, the data preparation part of the Service Center can be, but need not be, co-located with the web and database servers. Final storage of formatted content can be accomplished remotely.

Figure 7:
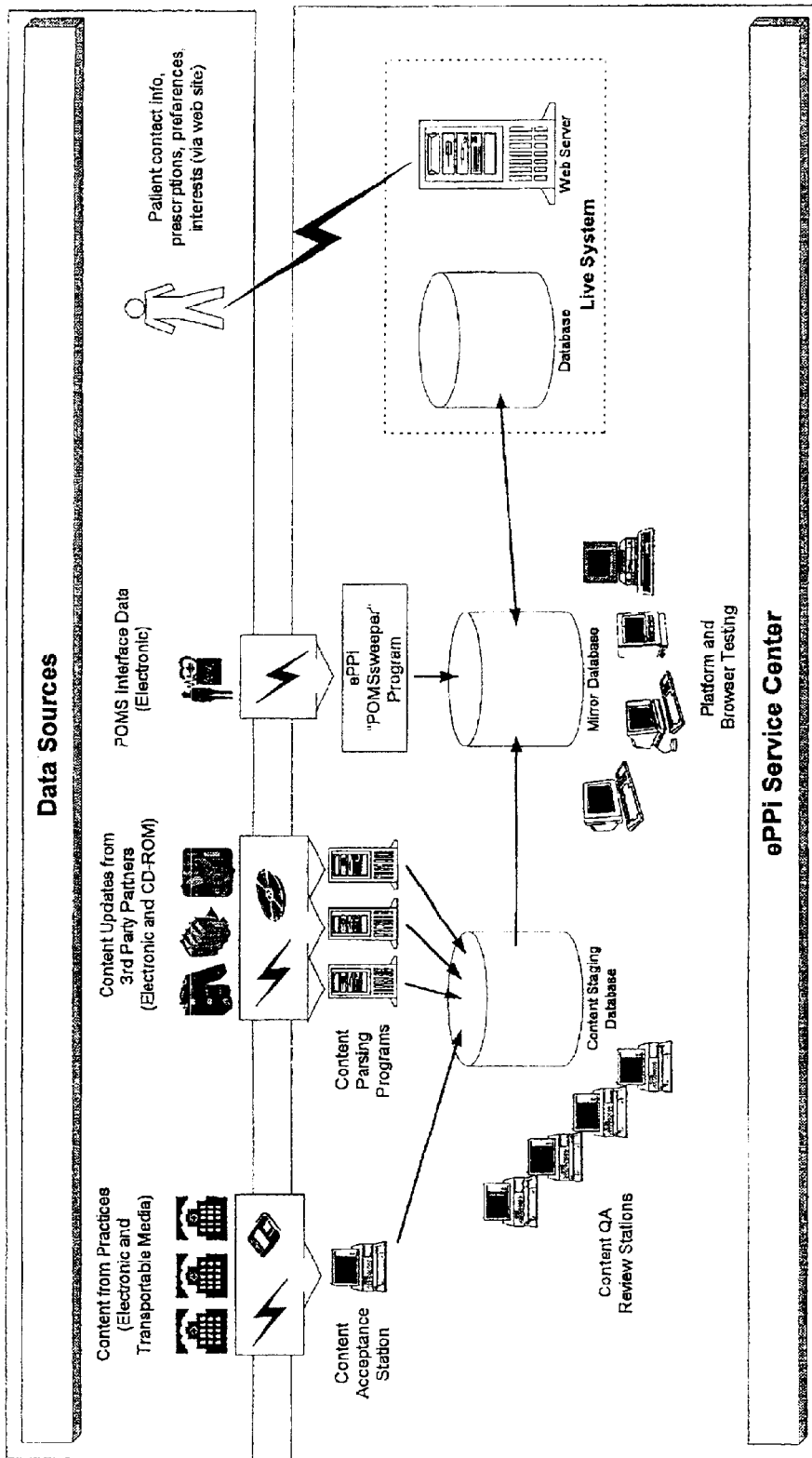
FIG. 7 is a conceptual diagram depicting the collection of data into the ePPi Service Center from various data sources and communicating the information between the practice and the patient.

FIG. 7 depicts the collection of data into the ePPi Service Center from its various sources. The collection of practice-specific content occurs largely at the start of the implementation of that practice's Web site. HTML designers format the content into static HTML pages, and store them in files in the Customer Domain, as previously described. Updates to practice-specific content occur as needed (for example, when practice staff or office policies change).

Updates to third party content occur periodically, on a schedule specific to each content provider. For example, one provider might send new content monthly; another might send it quarterly. Due to the predictable nature of these content updates, a parsing program can be constructed for each content provider, to filter the received content, evaluate the changes, and update the ePPi database automatically.

To handle the collection of patient-specific episodic information that drives customization of content to the patients, a dedicated program called the POMSSweeper checks ("sweeps") designated folders on the ePPi Service Center server(s) for data files and reports that have arrived from the Practice Office Management Systems (POMS)—the scheduling and billing systems of the various practices. The files arrive via e-mail or FTP (File Transfer Protocol) or any other transport mechanism which can place them into a designated folder on one of servers in the ePPi Service Center. The file transfers can occur daily, or more frequently if the practice desires.

Figure 8:
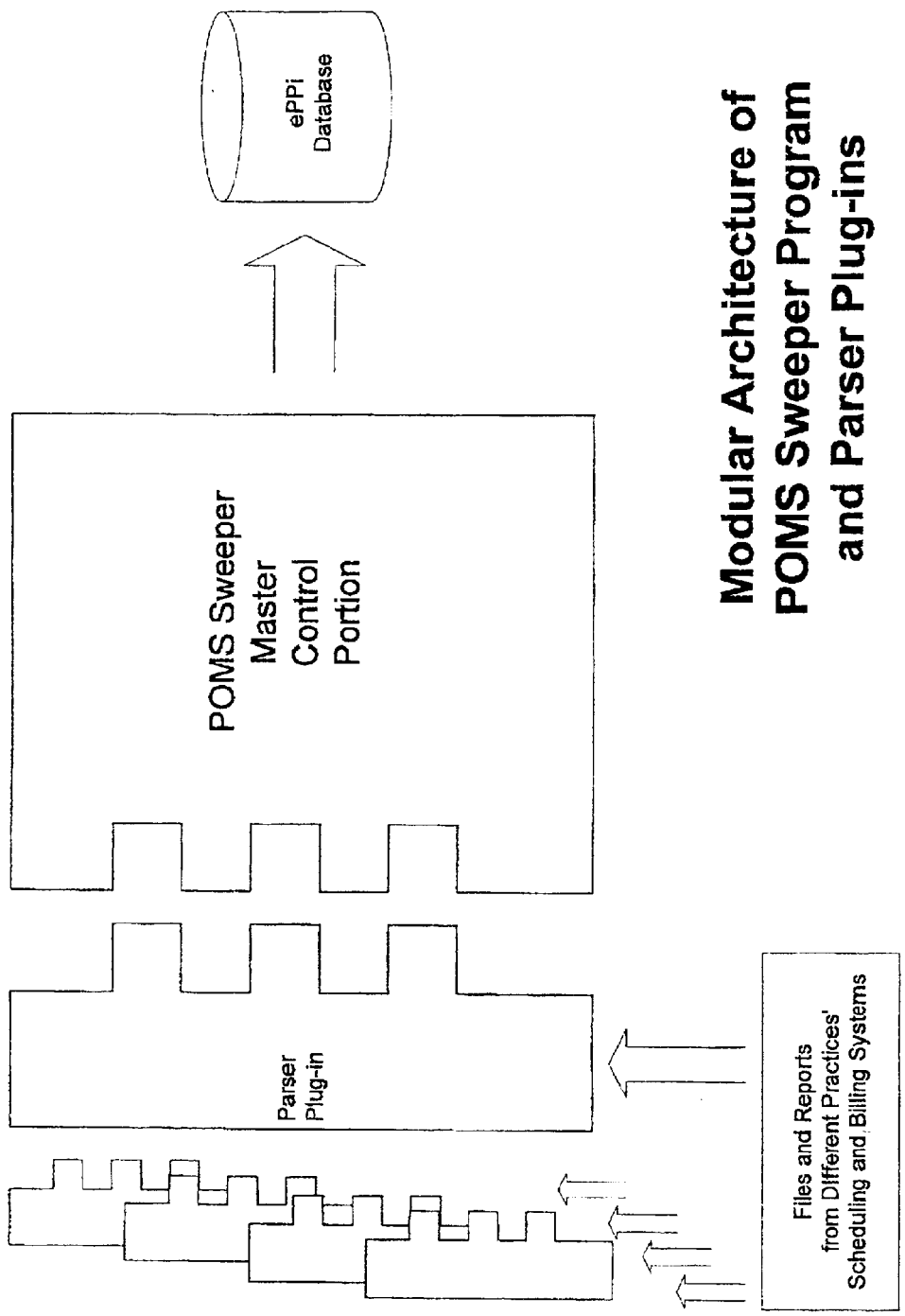
FIG. 8 is a conceptual diagram depicting the modular architecture of the POMSSweeper program, showing the relationship of parser plug-ins to master control portion.

The POMSSweeper program is designed in a modular architecture so that a variety of file and report formats (the output of the various POMS systems) can all be supported. As illustrated in FIG. 8, the architecture involves two basic components: a master control portion and a plug-in. A different plug-in corresponds to each file or report format (FIG. 8).

The master control portion of the POMSSweeper program contains the logic for sweeping the folders and identifying the source of the file transmission (client practice and POMS vendor). From this information, it makes the determination of which plug-in(s) to use to parse the file(s) as shown in FIG. 8.

After loading the proper plug-in, the master control portion makes iterative requests of the plug-in to provide data records in an established, generic format. Vendor-specific format details of the files and reports are totally transparent to the master control portion of the program. Thus, elements such as header records and trailer records are handled by the plug-in for that file type, and are not "seen" in their native form by the master control portion.

The master control portion accepts each transaction record from the plug-in and stores it in the ePPi database, where triggers and stored procedures realize the mapping of practice-specific or licensed third-party content to the individual patients.

In the initial embodiment of the invention, the following types of episodes or transactions are handled:

REG: a patient demographic record that populates the Repository table in the database to facilitate subsequent validation of the patient's sign-up (REGistration) request;

APPT: an APPoinTment that has been added, changed, or deleted for a patient to facilitate delivery of visit-specific content to the patient, as well as reminders of upcoming appointments; and TRAN: a post-visit TRANsaction report from the practice's billing system, containing industry standard ICD-9 and CPT-4 codes as used for insurance billing to facilitate delivery of post-visit instructions and recommended reading to the patient.

To support additional personalization, customization, and narrowcast of content to individual patients, additional types of transactions can be defined in the future, and are considered part of the original invention.

Figure 9:
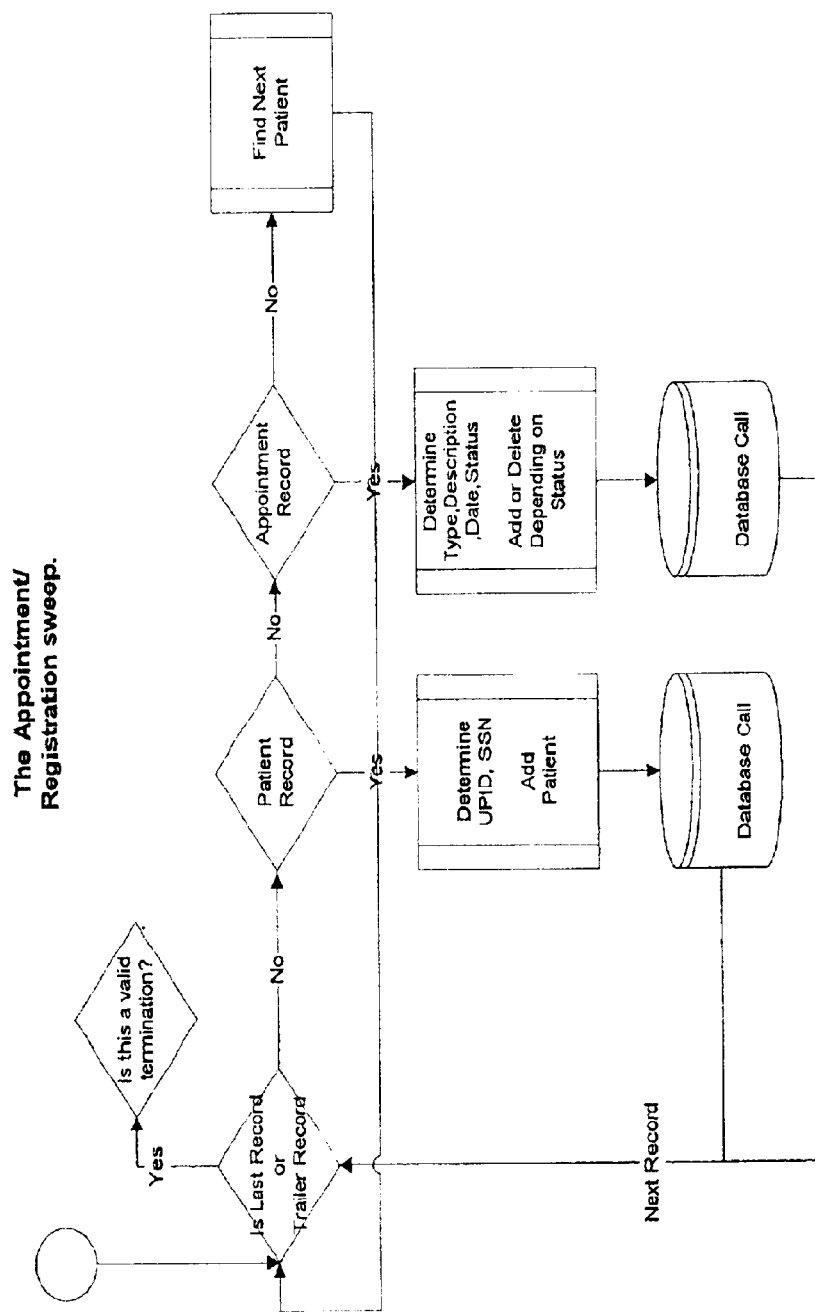
FIG. 9 is a conceptual diagram depicting the logical processing applied by the master control portion of the system for the Appointment/Registration sweep.
Figure 10:
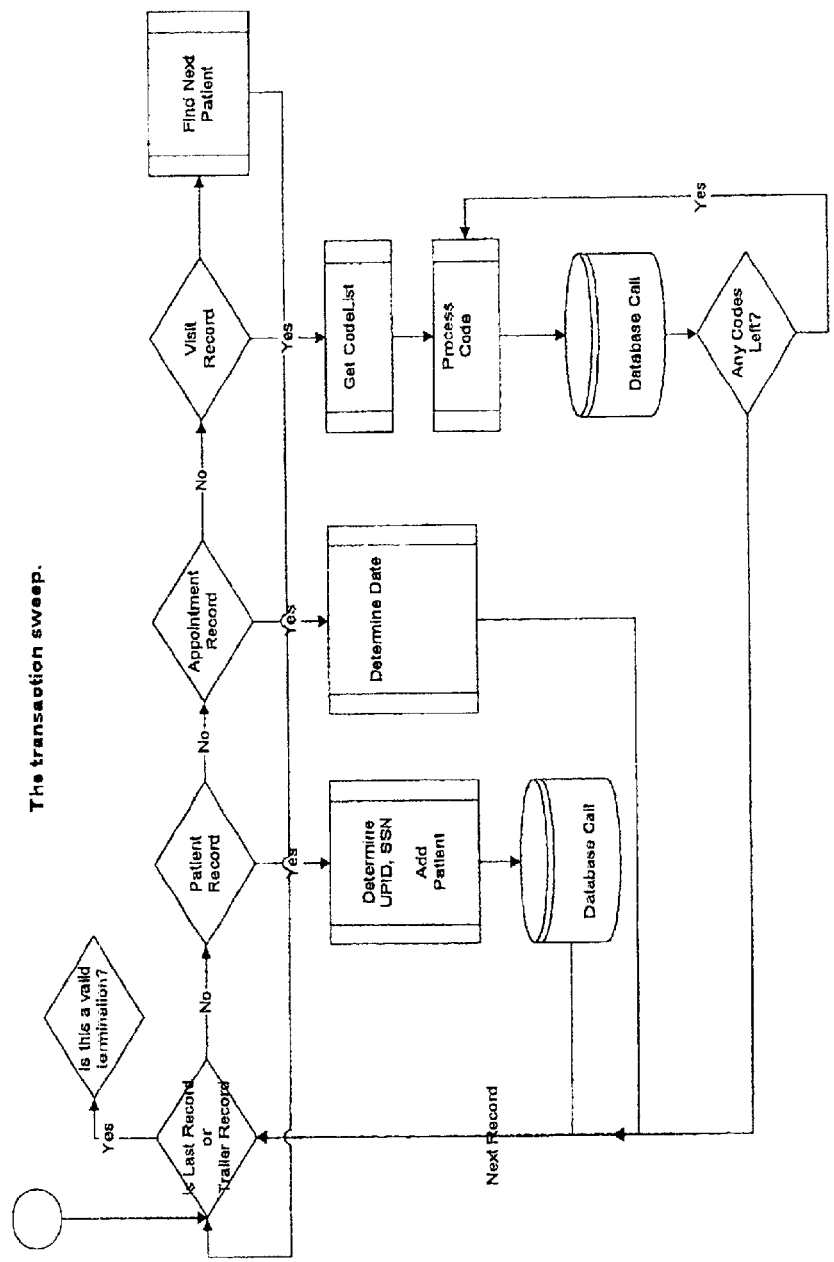
FIG. 10 is a conceptual diagram depicting the logical processing applied by the master control portion of the system for the Transactional sweep.

The logical processing applied by the master control portion for the three representative transaction types is illustrated in FIGS. 9 and 10, wherein FIG. 9 depicts the Appointment/Registration sweep, and FIG. 10 depicts the Transactional sweep. It should be noted that date is optional and when it is available, it only provides a context for the occurrence of the procedures and diagnoses.

The REG and APPT processing is identical because the patient population defined for registration validation purposes is based on the existence of appointment records for patients over an extended period. Furthermore, future appointments for the patient are kept in the Repository until the patient actually registers, so that customization of content occurs from the patient's very first login. Thus, the REG and APPT record formats can be identical.

In order to support multiple plug-ins for different file and report formats, the master control portion depends upon a class that is dynamically loaded and conforms to the specific object-oriented program interface. Through this object-oriented interface, the master control portion expects the plug-in to be able to supply the following six record types. Note that the information need not exist per se as a fixed field record in the file; it is the specific responsibility of the plug-in to return the record to the master control portion of the POMSSweeper in accordance with the class interface. This provides maximum flexibility in file and report formats; it is the plug-in that actually parses the report. Although the term "record" is used throughout this description, it is not intended to mean a physical record. The records could be created on the fly from a file that does not have the same structure as the required record. Any structure is suitable as long as it can be converted to the specified interface requirements.

The "system record" is responsible for initializing the data file. The properties are the FileSize and IFFile. The "FileSize" property is used to get the file size, and in conjunction with the average record size specified in a configuration file, to provide progress feedback through the application. The "IFFile" property is used to specify the file that contains the information. "NextRecord" is the method used to get to the next record of the data file.

All subsequent records contain the methods: IsLastRecord, NextRecord, RecordCount, and RecType. "IsLastRecord" determines if the end of the datafile has been reached. "NextRecord" moves the file cursor to the next record. "RecordCount" determines the cursor location and is used for determining application feedback. "RecType" returns a record type that must match a set of know record types for the current plug-in, as defined in a configuration file.

The first record after the system record is the header. This record has information that tags the report. For example, the report title, report version, and vendor could be used to verify the authenticity of the report. The plug-in can validate information at this point, and raise an exception to the sweep application in the event of failure. All reports can have only one header record.

The next record type is the patient. It supplies a context for following records. The property of "UPID" is the unique user identification number. The "SSN" is the social security number. Until a new patient record is found, the appointment and visit records will reference this patient within the sweep application.

The next record type is the appointment type. The "ApptStatus" property conveys the type of appointment activity. The type of appointment indicates if the appointment should be added or removed from the patient's scheduled appointments. This must also be coordinated with the list of appointment types for the current plug-in, as defined in a configuration file. The UPIN is the unique identifier for the physician associated with the appointment. The "ApptDate" is the date of the appointment. The "VisitType" and "VisitDes" are the reason codes and description for the appointment.

The next record type is the visit record. It is responsible for information about procedures or diagnoses that have occurred. The context of the visit is determined from the most recent patient record. Optionally, an appointment record may precede the visit record to determine when the procedure or diagnosis was made. The "DiagCode" property is a "comma delimited" list of diagnostic codes. The ProcCode is a comma delimited list of procedure codes. A "comma delimited" record is a layout that separates data fields with a comma and usually surrounds character data with quotes. The UPIN remains the unique physician's identifier number.

Figure 11:
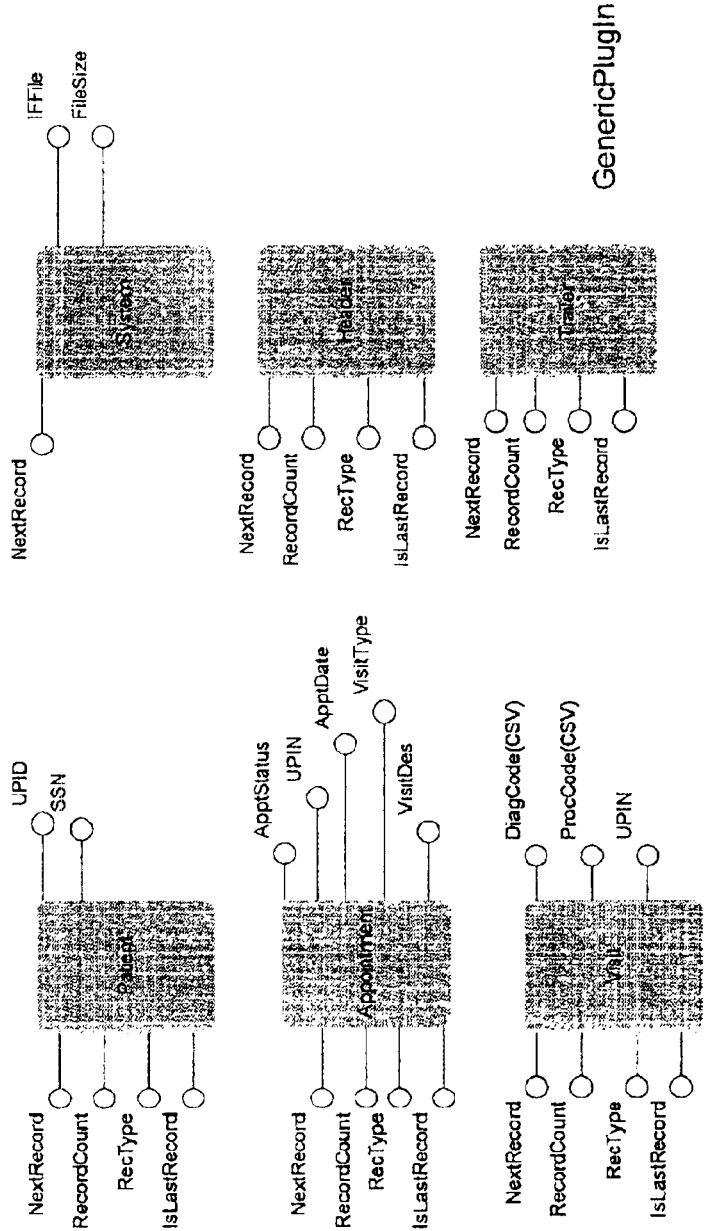
Figure 12:
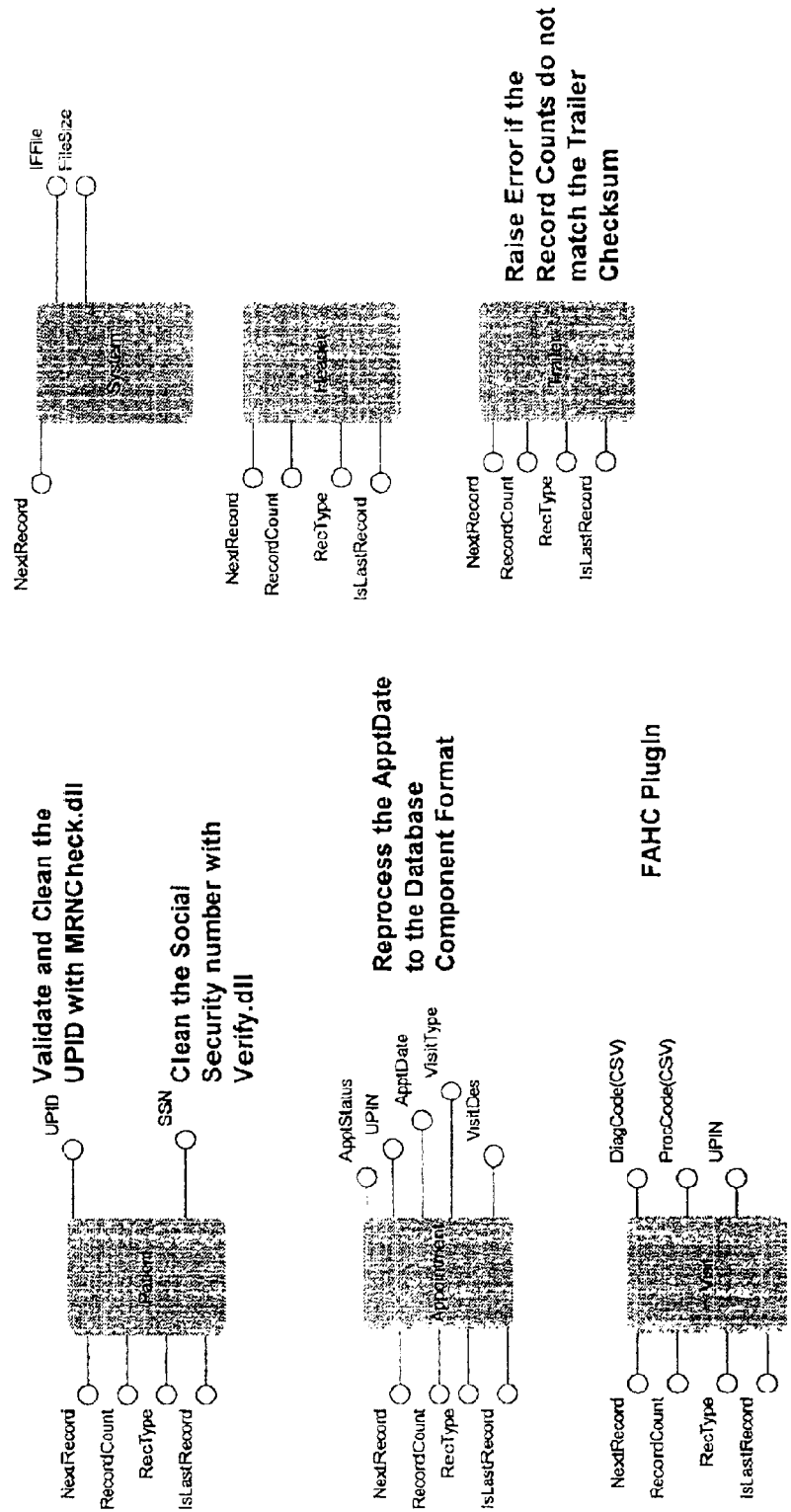
FIG. 12 is a conceptual diagram depicting the objects and applications of the Plug-In used in the ePPi system for the exemplary FAHC test site.

The final object type is the trailer record. Only one should exist, and it should be at the end of the report. It can be used to determine if the entire report was transferred. As with any of the objects, any integrity problems can be communicated to the sweep application by raising an error. The objects and application of a Plug-In are shown in FIG. 11 (a generic Plug-In) and FIG. 12 (the Plug-In used in the ePPi system for the exemplary FAHC test site). When compared with the generic Plug-In of FIG. 11, it is apparent that the Plug-In in FIG. 12 contains annotations regarding some of the business rules that were used to process the FAHC report. It further demonstrates the simplicity with which the ePPi system can be adapted by one of ordinary skill in the art for other practices and providers.

The sweep application handles all errors provided by the plug-in by trapping the error and logging the problem. Since this is a server application, every effort is made to recover from every error without disabling the application. The logged error is followed by a call to FindNextPatient. "FindNextPatient" tries to recover the error by looking for the first record that begins with a patient record type.

The database calls use a component that returns specific errors. Some errors are expected, such as duplicate patient records. Trapping these errors does not indicate a real error that requires a recovery.

There are two configuration files that drive the sweep application. The "POMSSweep" initialization file is used to point to the .INI file that contains the application. The design of pointing to another .INI file allows sharing of settings and load balancing of a sweep running on a different machine.

An example of the local initilization (.INI) file is:

[General]

MasterIniLocation=
  "K:\Work\POMSShared\MASTERPOMS. ini"

An example of the working initialization file appears, as follows:

[General]

ForwardRecipient="kilsen@eppi.com"

SweepDirectory="k:\POMS\"

;Practice Information Section

[FAHC]

Vendor="ABC"

Practice="Given Health Care"

; no spaces allowed in this list!!!

AddAptStatus="PEN,ARR,RSC"

; no spaces allowed in this list!!!

DelAptStatus="BMP,CAN,NOS"

;Title of the class to use

POMSSystem="GIVENIF32.PomsRecord"

;Recordtypes

HeadType="000"

PatType="100"

ApptType="200"

VisitType="300"

TrailType="999"

;Default Record Size

DefRecSize="152"

The "ForwardRecipient" is the mail address of someone who is responsible for reviewing the daily logs created by the sweep application. If an error recovery occurs, the ForwardRecipient is sent an email to check the daily log.

The "sweep directory" is the root level of the structure for the storage of the reports.

The "practice specific area," in this case "FAHC," identifies practice specific contents. This label must match the client name in the report title and the client folder in the storage structure.

The "vendor," in this case "ABC" is the creator of the POMS system that generates the reports.

The "practice" is the name of the practice that is known by the component that calls the database.

The "AddAptStatus" value is a list of appointment activity types that result in a call to the database to add an appointment to the patient's records. This value must be a comma delimited list without any spaces.

The "DelAptStatus" value is a list of appointment activity types that result in a call to the database to remove an appointment from the patient's records. This value is also a comma delimited list without any spaces.

The "POMSSystem" is the name of the class used to evaluate a report for the selected practice. It is dynamically loaded as the client of the report is determined.

The "record types" section identifies the record type values that the POMSSystem returns as the records are parsed.

The "default record size" is the most likely record length in units that are specific to the practice. It is used in conjunction with the FileSize property of the System object of the POMSSystem, and the RecordCount of all of the objects to determine the progress feedback on the user interface.

Together, the configuration file and the practice/vendor-specific plug-in enable the POMSSweeper application to read and process files from a particular POMS source. However, those files must be exported from the POMS scheduling and billing systems, according to specifications that ensure that the files can be read by the particular plug-in.

Although the initial users of the ePPi system Web site are patients, the invention is capable of, and intended to include, service to other types of users/roles, including: doctors; Practice Administrators and other administrators. Practice Administrators will have direct edit capability to post new content items directly to the database. This can be readily accomplished through the use of a form similar (or identical) to the one used for content QA review in the Service Center, but presented via the Web. The Practice Administrator can then type in (or cut and paste) the content item, title, start and end display dates, as well as identify the content item as a news item/hot topic/frequently asked question. Practice Administrators will also be able to edit and remove individual practice content items.

A similar direct entry/edit capability is possible for practice-specific instructions, drug information, and articles. In addition to providing articles for the exclusive benefit of their patients, and specialized instructions/drug information, practices also have the ability to suppress individual articles, instructions, or drug information from the ePPi general database, with or without replacement. To support this feature, a "censor" mechanism is added to the database, the Service Center, and the practice administrator feature set.

Finally, the on-going use of the Web site by large numbers of patients represents a valuable source of information for the practice. Additional procedures can analyze patient usage patterns, most commonly viewed content items, most commonly selected areas of interest, etc. This information can be compiled into a report and transmitted to the practice, or to third parties, using the same code numbers for collecting the data and same delivery mechanisms as disclosed for health tracking and other patient form data (i.e., e-mail or FAX).

The present invention is further described in the following examples. These examples are not to be construed as limiting the scope of the appended claims.

EXAMPLES

The following examples were developed through testing of the ePPi system at a selected test site (FAHC).

Example 1

The POMS Interface Specification

In this case, the plug-in and specification were developed in order to facilitate convenient extraction of data from the specific scheduling and billing systems in place at the test site. These scheduling and billing systems happened to be developed by the POMS vendor IDX Systems, Inc. Although intended to be only exemplary, subsequent practices using the POMS systems from the same provider can use the same specification to create data files that are readable by the same plug-in, a representative example of which follows:

1. In order to automate the process of populating and updating the ePPi database with patient and appointment information, the practice provided responses to the following instructions to provide the system with the necessary data to permit development of a plug-in.

To generate records of all patients having the following criteria:

The patient has appointments (future or 2 years in the past) with an ePPi registered provider.

An ePPi registered provider is one that has been defined as such in the practice system. An internal reference of patients on the practice system is also updated to keep track of the patients sent to the ePPi Service Center.

The logic searches the patient database, extracting demographic and appointment data for all patients having appointments in the future or within the past date range period with an ePPi registered provider. A date two years in the past from the current system date will default. The user can override this date. However, the date entered cannot be a future date. A file (filename to be determined) is created and placed in a specified directory. Practice personnel are responsible for getting the file to the ePPi Service Center (via FTP or e-mail).

The file contains the following records:

Header Record
   Patient record (one per patient)
   Appointment record (repeating, one per appointment)

2. Real-time triggers were added to the system to capture demographic updates for patients contained in the internal reference as well as appointment schedules, arrivals, cancels and reschedules. When one of the above occurs, the system checks the internal reference for the patient data. If so, the event is filed into the outbound queue. If not, and the trigger event is appointment related, the system checks to verify whether the appointment is with an ePPi registered provider. If so, the event is filed into the outbound queue and the patient added to the internal reference. If not, no event is filed.

Although the events were triggered real-time, the data is compiled, resulting in the creation of a file (filename to be determined).

The file contains the following records:

Header Record
   Patient record (one per patient)
   [Appointment record (one per appointment)]

3. The billing system is used to capture diagnosis and procedure code data. A process is created, which runs nightly through the day's billing records collecting charge data based upon the following criteria:

The patient is listed in the internal index, the invoice contains at least one charge transaction and the Billing Provider specified on the invoice is an ePPi registered provider.

An ePPi registered provider is one that has been defined as such in the practice system. If the patient is not in the internal index, the invoice does not contain at least one charge transaction or the Billing Provider is not an ePPi registered provider, no data for that patient invoice is captured. Once the data is collected, a file (filename to be determined) containing patient demographics, appointment information (if an appointment is linked to the invoice) and charge transaction data is created.

The file contains the following records:

Header Record
    Patient record (one per patient)
        [Appointment record (one per appointment)]
        Transaction record (one per invoice)

| Position | Description | Format |
|---|---|---|
| 4. The Record Layouts Header Record-000 | | |
| 1–3 | Record type | 000 |
| 4–11 | Processing date | MMDDYYYY |
| 12–61 | Client name (vendor type, version) | LJBF, free text |
| 62–150 | Not used | Blank filled |
| Trailer Record-999 | | |
| 1–3 | Record type | 999 |
| 4–10 | Record count (total number of records including Header and Trailer) | RJZF |
| 11–17 | 100 Record count (total number of patient records) | RJZF |
| 18–24 | 200 Record count (total number of appointment records) | RJZF |
| 25–31 | 300 Record count (total number of transaction records) | RJZF |
| 32–150 | Not used | Blank filled |
| Patient Record | | |
| 1–3 | Record type | NNN |
| 4–15 | Unique patient identifier | LJBF |
| 16–26 | Social security number | NNN-NN-NNNN |
| 27–34 | Date of birth | MMDDYYYY |
| 35 | Gender | M, F or I |
| 36–150 | Not used | Blank filled |
| Appointment Record | | |
| 1–3 | Record type | NNN |
| 4–15 | Unique Patient Identifier | LJBF |
| 16–27 | Appointment date/time | MMDDYYYYHHMM |
| 28–35 | Appointment Number | RJZF |
| 36–38 | Appointment Status | LJBF |
| 39–43 | Visit Type | LJBF |
| 44–63 | Visit Type Description | LJBF |
| 64–69 | Provider ID | LJBF |
| 70–117 | Provider Name | LJBF |
| 118–150 | Not used | Blank filled |

| Position | Description | Format |
|---|---|---|
| Transaction Record | | |
| 1–3 | Record type | NNN |
| 4–15 | Unique Patient Identifier | LJBF |
| 16–21 | Billing Provider UPIN | LJBF |
| 22–69 | Billing Provider Name | LJBF |
| 70–* | Header Diagnosis Codes (Dx1, Dx2, . . . , DxN); | CSV with ; at end |
| * | Procedure Codes (Proc1,Proc, . . . , ProcN); | CSV with ; at end |

A more generic interface requirement specification follows as Example 2, which has been delivered to ePPi test client practices to facilitate their generation of files containing the REG, APPT, and TRAN information.

Example 2 ePPi/Practice Interface Specification

To automate the process of populating and updating the ePPi database with patient and appointment information, the Practice can deliver the following data:

1. A periodic (e.g., daily) file containing information about scheduled APPOINTMENTS for patients. The relevant details for each appointment include the patient identifier, the provider (doctor, etc.) identifier, the date/time, and the visit type.

2. A periodic (e.g., daily) file containing information about billing TRANSACTIONS for patient visits that have occurred. The relevant details for each transaction include the patient identifier, the provider (doctor, etc.) identifier, the date/time, the diagnosis code(s) for the visit, and the procedure code(s) for the visit.

3. A file to support the ePPi REGISTRATION process, containing information about patients of providers who are contracting to use the ePPi service, with all known upcoming appointments for those patients. This file was supplied at the start of the project, and is again provided whenever new providers are added.

The preferred delivery mechanism is FTP. Each practice is provided an FTP account and password, as well as a port number, unique to the client.

The name of the file determines the processing flow once it arrives at the ePPi Service Center. The format is: Client_InterfaceVendor_ReportType_Date, wherein the portions of the name are defined in TABLE 4 as follows:

TABLE 4 describing file naming format

| File Name | Description |
|---|---|
| Client | A unique identifier for the client, as agreed to by the client and the ePPi Service Center personnel |
| Interface-Vendor | An identifier for the vendor of the Interface used to generate the data files, as agreed to by the client, the vendor, and the ePPi Service Center personnel |
| ReportType | Appts = an APPOINTMENTS file; Tran = a TRANSACTION file; Reg = a REGISTRATION file |

TABLE 4-continued describing file naming format

| File Name | Description |
|---|---|
| Date | The date when the Interface created the file, in the format YYYYMMDDHHMM. This assures that the filename is unique. HH is the hour in military time, i.e., 00–23. |

Each file consists of a series of fixed length records. Each record is 150 characters and is terminated by a CR/LF. The first 3 characters of each record identify the RECORD TYPE. There are five record types:

000: Header
999: Trailer
100: Patient
200: Appointment
300: Transaction

1. Header Record

The "header" is present to confirm the contents of the file. It contains the same information as the file name, as well as the version of the Interface (see TABLE 5). There can only be one header record and it must be the first one in the file.

TABLE 5 the Header Record.

| Position | Description | Format |
|---|---|---|
| 1–3 | Record type | 000 |
| 4–11 | Processing date | YYYYMMDD |
| 12–61 | Client/Interface/Report/Date/Version | Client_InterfaceVendor_ReportType_Date_Version (i.e., same as file name, plus a version identifier) |
| 62–150 | Not used | Blank filled |

2. Trailer Record

The "trailer" identifies the end of the file and includes checksum values that allow a validation of the number of records (see TABLE 6).

TABLE 6 the Trailer Record.

| Position | Description | Format |
|---|---|---|
| 1–3 | Record type | 999 |
| 4–10 | Record count (total number of records including Header and Trailer) | RJZF |
| 11–17 | 100 Record count (total number of patient records) | RJZF |
| 18–24 | 200 Record count (total number of appointment records) | RJZF |
| 25–31 | 300 Record count (total number of transaction records) | RJZF |
| 32–150 | Not used | Blank filled |

3. Patient Record

The "patient record" identifies the patient context of the following records. The fields include a unique patient identifier, a secondary identifier such as social security number, the date of birth, and the gender (see TABLE 7). Subsequent records (appointments and visits) relate to this patient unless overridden by the appointment record. This identifies the new patients, as well as relate the patients to appointments and transactions.

TABLE 7 the Patient Record.

| Position | Description | Format |
|---|---|---|
| 1–3 | Record type | 100 |
| 4–15 | Unique patient identifier | LJBF |
| 16–26 | Social security number | NNN-NN-NNNN |
| 27–34 | Date of birth | YYYYMMDD |
| 35 | Gender | M, F or I |
| 36–150 | Not used | Blank filled |

4. Appointment Record

The "appointment record" identifies the time and reason for an appointment, the status, and the doctor to be seen (see TABLE 8). The status field indicates if the appointment is an additional appointment or one that should be deleted. The appointment record is generally triggered by the activity in the practice's scheduling system.

TABLE 8 the Appointment Record.

| Position | Description | Format |
|---|---|---|
| 1–3 | Record type | 200 |
| 4–15 | Unique Patient Identifier | LJBF |
| 16–27 | Appointment date/time | YYYYMMDDHHMM |
| 28–35 | Appointment Number | RJZF |
| 36–38 | Appointment Status | LJBF |
| 39–43 | Visit Type | LJBF |
| 44–63 | Visit Type Description | LJBF |
| 64–69 | Provider ID | LJBF |
| 70–117 | Provider Name | LJBF |
| 118–150 | Not used | Blank filled |

The 3-character Appointment Status ultimately indicates whether the record should be ADDED to the ePPi database, or DELETED. The actual values are configurable, and it is perfectly fine if there are multiple values that have slightly different connotations on the practice side, but which all mean the same thing to the ePPi side.

For example, BMP ("bump"), CAN ("cancel"), and NOS ("no show") could all mean DELETE.

5. Transaction Record

The "transaction record" identifies the specific diagnosis and/or procedure codes for a patient visit (see TABLE 9). The transaction record is generally triggered by the activity in the practice's billing system. Thus, it includes information about the doctor, but does not contain the details about the appointment date and time.

TABLE 9 the Transaction Record.

| Position | Description | Format |
|---|---|---|
| 1–3 | Record type | 300 |
| 4–15 | Unique Patient Identifier | LJBF |
| 16–21 | Billing Provider UPIN | LJBF |
| 22–69 | Billing Provider Name | LJBF |
| 70–* | Diagnosis Codes (Dx1, Dx2, . . . , DxN); | CSV with ; at end |
| * | Procedure Codes (Proc1, Proc, . . . , ProcN); | CSV with ; at end |

The record types that are present in a file depend on the file type.

1. Appts File

The Appts file (containing patient appointment information) begins with a Header record, and ends with a Trailer record. Patient appointments are denoted in the file by a Patient record, followed by one or more Appointment records relating to that patient. Appointments for a different patient are denoted by the presence of a different Patient record, in turn followed by one or more Appointment records.

For example:

000 (Header record)

100 (Patient record for patient A)

200 (Appointment record 1 for patient A)

200 (Appointment record 2 for patient A)

100 (Patient record for patient B)

200 (Appointment record 1 for patient B)

100 (Patient record for patient C)

200 (Appointment record 1 for patient C)

999 (Trailer record)

2. Tran File

The Tran file (containing transaction information from the billing system, including diagnostic and procedure codes) begins with a Header record, and ends with a Trailer record. Patient visits transactions are denoted in the file by a Patient record, optionally followed by an Appointment record, which is then followed by a Transaction record. Although it is common for an Appointment record to be present, it is not mandatory (some transactions triggered by the practice billing system may not necessarily have an associated appointment).

For example:

000 (Header record)

100 (Patient record for patient A)

200 (Appointment record 1 for patient A)

300 (Transaction record for patient A, appointment 1)

200 (Appointment record 2 for patient A)

300 (Transaction record for patient A, appointment 2)

100 (Patient record for patient B)

300 (Transaction record 1 for patient B; no appointment details)

300 (Transaction record 2 for patient B; no appointment details)

999 (Trailer record)

3. Reg File

The Reg file (used to support the registration process) begins with a Header record, and ends with a Trailer record. A Patient record is present for each patient; these patients are deemed "permitted" to use the ePPi system by virtue of their doctor's identity. Optionally, a Patient record may also be followed by one or more Appointment records. If present, the details of these appointments are stored in a repository until the patient first signs on to the ePPi system, at which time their upcoming appointments are moved to the "active" database and shown on his/her personal web page.

For example 000 (Header record)

100 (Patient record for patient A)

100 (Patient record for patient B)

200 (Appointment record 1 for patient B)

200 (Appointment record 2 for patient B)

200 (Appointment record 3 for patient B)

200 (Appointment record 4 for patient B)

200 (Appointment record 5 for patient B)

100 (Patient record for patient C)

999 (Trailer record)

4. Interface Logic: Identification of ePPi Registered Providers

At a practice with many providers, not all of the providers necessarily participate in the ePPi online service. A mechanism must be put in place to identify which providers are participating. The ePPi Service Center requires a list from each group practice to supply the unique provider numbers for all such providers within the practice.

From time to time, new providers might need to be added to this list. For example, another office location might begin to participate, requiring that all providers at that location be added. Or, a new provider might join the practice and need to be added individually.

Whenever new providers are added, in addition to the identification of the provider(s), a new Reg file is generated for the patients of those providers.

5. Selection of Patients for the Reg File

A filter is used to determine the patients of a provider or a subset of providers in order to build the Reg file. The preferred filter criteria are:

The patient has future appointments scheduled with the provider

OR

The patient has had an appointment with the provider within the last 2 years.

6. Internal Reference of ePPi Patients

Once a patient has been selected for inclusion in a Reg file, that patient is included in an internal reference. Subsequently, the appointment and billing activity can be checked against that reference to determine if the activity occurred for an "ePPi patient" and therefore if the records need to be sent to the ePPi Service Center.

7. Selection of Records for the Appts File

Activity in the scheduling system results in the creation of Appointment records, based on the following criteria:

The patient is in the internal reference of "ePPi Patients"

AND

The provider is an "ePPi Registered Provider."

8. Selection of Records for the Tran File

Activity in the billing system results in Transaction records being created, based on the following criteria:

The patient is in the internal reference of "ePPi Patients"

AND

The provider is an "ePPi Registered Provider."

In addition, since the purpose of sending the Tran file is to use the diagnostic and procedure codes to populate the patient's web page with relevant information, it is only logical that billing transactions containing no diagnostic or procedure codes need not be sent.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the basic principles of the invention. Such modifications and additional embodiments are also intended to fall within the scope and spirit of the appended claims.

What is claimed is:

1. A method of automatically and electronically communicating between at least one health-care provider and a plurality of users serviced by the health-care provider, said method comprising the steps of:

initiating a communication by one of the plurality of users to the provider for information, wherein the provider has established a preexisting medical record for each user;

enabling communication by transporting the communication through a provider/patient interface over an electronic communication network to a Web site which is unique to the provider, whereupon the communication is automatically reformatted and processed or stored on a central server, said Web site supported by or in communication with the central server through a provider-patient interface service center;

electronically comparing content of the communication with mapped content, which has been previously provided by the provider to the central server, to formulate a response as a static or dynamic object, or a combined static and dynamic object; and returning the response to the communication automatically to the user's computer, whereupon the response is read by the user or stored on the user's computers said provider/patient interface providing a fully automated mechanism for generating a personalized page or area within the provider's Web site for each user serviced by the provider; and said patient-provider interface service center for dynamically assembling and delivering custom content to said user.

2. The method of claim 1, wherein the method is implemented by an electronic provider-patient interface system (the "ePPi system").

3. The method of claim 1, wherein when the user's communication includes a request for information or relates to an episodic event, the method further comprises the additional step of:

notifying the provider and the user automatically that information response has been sent to the provider's and the user's computers, respectively.

4. The method of claim 1, wherein the central server comprises: a Web server capable of responding to HTTP requests; a database server capable of maintaining complex relationships between users and information content; and a modular data collection program capable of receiving information as coded data from practices in a variety of different formats, and reformatting and storing the information.

5. The method of claim 4, wherein the central server further comprises an electronic mailing capability to support the automated transmission of notifications to users or providers.

6. The method of claim 1, wherein there are one or more providers, each of which is in communication with a plurality of users.

7. The method of claim 1, wherein the communications network is either an internet or intranet network selected from the group consisting essentially of Internet, World Wide Web, telephone network, coaxial or fiber cable network, radio wave network, infrared radiation network, ATM link, FDDI link, satellite link, twisted pair fiber-optic broadcast wireless or other wireless network, LAN, WAN, and standard Ethernet link.

8. The method of claim 7, wherein the communications network is the Internet.

9. The method of claim 1, wherein delivery occurs over the World Wide Web.

10. The method of claim 9, wherein the delivery is in HTML format.

11. The method of claim 1, wherein custom content is assembled using Active Server Pages (ASP) technology.

12. The method of claim 1, wherein the custom content is selected from a library of information, and wherein the selection is based upon specific data received from the provider about each user served by the provider.

13. The method of claim 12, wherein the data about each user comprises information about each user's visits to the provider.

14. The method of claim 12, wherein the selection is based upon logical mappings that reside in a database server capable of maintaining complex relationships.

15. The method of claim 1, further comprising a unique provider's Web site for each of the one or more providers, wherein each Web site is supported by or in communication with the central server through the Service Center.

16. The method of claim 1, wherein at least one provider's Web site and at least one user's computer are hyperlinked through the provider/patient interface.

17. The method of claim 1, wherein communications, requests, notifications and submissions of information from one or more providers and from the users of the electronic communications system are in standardized formats.

18. The method of claim 17, wherein the standardized formats are derived from standard administrative and billing codes used by the provider.

* * * * *

UNITED STATES PATENT AND TRADEMARK OFFICE
CERTIFICATE OF CORRECTION

PATENT NO. : 6,757,898 B1
APPLICATION NO. : 09/484550
DATED : June 29, 2004
INVENTOR(S) : Ilsen et al.

It is certified that error appears in the above-identified patent and that said Letters Patent is hereby corrected as shown below:

Column 13,
Line 10, "development tools could include CGI, Pert, Java, TCL, and" should read --development tools could include CGI, Perl, Java, TCL, and--.

Column 14,
Line 10, "branding options,for the practice Web site, and transmits the" should read --branding options for the practice Web site, and transmits the--.

Column 17,
Line 31, "ePPi "link libraries" automatically deliver content to each" should read --ePPi "link libraries") automatically deliver content to each--.

Column 20,
Line 57, "TABLE 1, the Patient View component: allows patients to" should read --TABLE 1, the Patient View component allows patients to--.

Column 26,
Lines 46, 47, 48, 49, "graphical elements include form buttons (such as "Login," "Sign Up," "Preview", navigation buttons ("Go to Top of Page", indicators ("New," "Recommended by Your Doctor" and any other graphical" should read --graphical elements include form buttons (such as "Login," "Sign Up," "Preview"), navigation buttons ("Go to Top of Page"), indicators ("New," "Recommended by Your Doctor") and any other graphical--.

Column 29,
Line 36, "E. Security Features p Much of the content presented" should read
--E. Security Features
Much of the content presented--
(Note that a hard new-line was omitted, and instead a letter "p" was inserted.)

Column 30,
Line 13, "various demographic information, to including, but not" should read --various demographic information, including, but not--.

Column 32,
Lines 59-60, "as follows: lowest tier database; middle tier=component, and top tier=ASP pages." should read --as follows: lowest tier=database; middle tier=component, and top tier=ASP pages.--.

UNITED STATES PATENT AND TRADEMARK OFFICE
CERTIFICATE OF CORRECTION

PATENT NO. : 6,757,898 B1
APPLICATION NO. : 09/484550
DATED : June 29, 2004
INVENTOR(S) : Ilsen et al.

It is certified that error appears in the above-identified patent and that said Letters Patent is hereby corrected as shown below:

Column 39,
Line 30, the section title "4. The Record Layouts" appears inside the table. It should appear BEFORE the table (i.e., above the column headings).

Column 45,
Line 16, "read by the user or stored on the user's computers" should read --read by the user or stored on the user's computer,--.

Column 46,
Line 34, "claim 1" should read --claim 15--.

Signed and Sealed this

Twentieth Day of February, 2007

JON W. DUDAS
*Director of the United States Patent and Trademark Office*